US011690720B2

(12) United States Patent
Alexander

(10) Patent No.: US 11,690,720 B2
(45) Date of Patent: *Jul. 4, 2023

(54) SYSTEMS AND METHODS FOR TREATING CARDIAC DYSFUNCTION

(71) Applicant: Edwards Lifesciences Corporation, Irvine, CA (US)

(72) Inventor: Miles D. Alexander, Menlo Park, CA (US)

(73) Assignee: EDWARDS LIFESCIENCES CORPORATION, Irvine, CA (US)

( * ) Notice: Subject to any disclaimer, the term of this patent is extended or adjusted under 35 U.S.C. 154(b) by 211 days.

This patent is subject to a terminal disclaimer.

(21) Appl. No.: 16/997,634

(22) Filed: Aug. 19, 2020

(65) Prior Publication Data

US 2020/0375743 A1 Dec. 3, 2020

Related U.S. Application Data

(63) Continuation of application No. 15/506,562, filed as application No. PCT/US2015/050827 on Sep. 18, 2015, now Pat. No. 10,751,183.

(30) Foreign Application Priority Data

Sep. 28, 2014 (CN) .......................... 201420564242.9
Sep. 28, 2014 (CN) .......................... 201420564806.9
Sep. 28, 2014 (CN) .......................... 201420564809.2

(51) Int. Cl.
*A61F 2/24* (2006.01)
*A61B 17/12* (2006.01)
(Continued)

(52) U.S. Cl.
CPC ...... *A61F 2/2487* (2013.01); *A61B 17/12036* (2013.01); *A61B 17/12122* (2013.01);
(Continued)

(58) Field of Classification Search
CPC .... A61F 2/2487; A61F 2/2436; A61F 2/9525; A61F 2/9522; A61F 2210/0014;
(Continued)

(56) References Cited

U.S. PATENT DOCUMENTS 3,874,388 A 4/1975 King et al.
4,007,743 A 2/1977 Blake
(Continued)

FOREIGN PATENT DOCUMENTS

CN 204169959 U 2/2015
EP 1474032 A2 11/2004
(Continued)

OTHER PUBLICATIONS

AGA Medical Corporation, www.amplatzer.comproducts. "The Muscular VSD Occluder" and "The Septal Occluder" device description. Accessed Apr. 3, 2002.
(Continued)

*Primary Examiner* — Paul B Prebilic
(74) *Attorney, Agent, or Firm* — Snell & Wilmer

(57) ABSTRACT

A system for treating cardiac dysfunction can include an expandable device for insertion into a heart, a foot configured to contact a portion of the heart, a support frame, and a membrane coupled to the support frame. The support frame can include a plurality of radially expandable struts each having a first free end configured to extend beyond the foot and a second end coupled to the foot. The plurality of radially expandable struts can include a plurality of staggered stops, and each of the stops can be positioned on a respective one of the struts proximal to the first free end of the respective one of the struts. Method for treating cardiac dysfunction can include implanting the systems described herein into a chamber of the heart.

15 Claims, 13 Drawing Sheets

(51) Int. Cl.
*A61F 2/95* (2013.01)
*A61B 17/00* (2006.01)
*A61B 17/064* (2006.01)

(52) U.S. Cl.
CPC .. *A61B 17/12145* (2013.01); *A61B 17/12168* (2013.01); *A61F 2/9525* (2020.05); *A61B 2017/0053* (2013.01); *A61B 2017/0641* (2013.01); *A61B 2017/1205* (2013.01); *A61F 2/2436* (2013.01); *A61F 2/9522* (2020.05); *A61F 2210/0014* (2013.01); *A61F 2220/0041* (2013.01); *A61F 2230/0093* (2013.01)

(58) Field of Classification Search
CPC ...... A61F 2220/0041; A61F 2220/0075; A61F 2230/0093; A61B 17/12036; A61B 2017/1205; A61B 17/12122; A61B 17/12145; A61B 2560/0456; A61B 2217/002; A61B 2560/04
See application file for complete search history.

(56) References Cited

U.S. PATENT DOCUMENTS

| | | |
|---|---|---|
| 4,425,908 A | 1/1984 | Simon |
| 4,453,545 A | 6/1984 | Inoue |
| 4,536,893 A | 8/1985 | Parravicini |
| 4,588,404 A | 5/1986 | Lapeyre |
| 4,619,246 A | 10/1986 | Molgaard-Nielsen et al. |
| 4,685,446 A | 8/1987 | Choy |
| 4,710,192 A | 12/1987 | Liotta et al. |
| 4,819,751 A | 4/1989 | Shimada et al. |
| 4,830,003 A | 5/1989 | Wolff et al. |
| 4,832,055 A | 5/1989 | Palestrant |
| 4,917,089 A | 4/1990 | Sideris |
| 4,983,165 A | 1/1991 | Loiterman |
| 5,104,399 A | 4/1992 | Lazarus |
| 5,192,301 A | 3/1993 | Kamiya et al. |
| 5,192,314 A | 3/1993 | Daskalakis |
| 5,258,000 A | 11/1993 | Gianturco |
| 5,375,612 A | 12/1994 | Cottenceau et al. |
| 5,385,156 A | 1/1995 | Oliva |
| 5,389,087 A | 2/1995 | Miraki |
| 5,425,744 A | 6/1995 | Fagan et al. |
| 5,433,727 A | 7/1995 | Sideris |
| 5,451,235 A | 9/1995 | Lock et al. |
| 5,496,277 A | 3/1996 | Termin et al. |
| 5,527,337 A | 6/1996 | Stack et al. |
| 5,527,338 A | 6/1996 | Purdy |
| 5,549,621 A | 8/1996 | Bessler et al. |
| 5,551,435 A | 9/1996 | Sramek |
| 5,578,069 A | 11/1996 | Miner, II |
| 5,634,936 A | 6/1997 | Linden et al. |
| 5,634,942 A | 6/1997 | Chevillon et al. |
| 5,647,870 A | 7/1997 | Kordis et al. |
| 5,702,343 A | 12/1997 | Alferness |
| 5,702,441 A | 12/1997 | Zhou |
| 5,709,707 A | 1/1998 | Lock et al. |
| 5,746,734 A | 5/1998 | Dormandy, Jr. et al. |
| 5,758,664 A | 6/1998 | Campbell et al. |
| 5,791,231 A | 8/1998 | Cohn et al. |
| 5,797,849 A | 8/1998 | Vesely et al. |
| 5,797,960 A | 8/1998 | Stevens et al. |
| 5,800,457 A | 9/1998 | Gelbfish |
| 5,800,517 A | 9/1998 | Anderson et al. |
| 5,829,447 A | 11/1998 | Stevens et al. |
| 5,833,682 A | 11/1998 | Amplatz et al. |
| 5,833,698 A | 11/1998 | Hinchliffe et al. |
| 5,836,968 A | 11/1998 | Simon et al. |
| 5,843,170 A | 12/1998 | Ahn |
| 5,860,951 A | 1/1999 | Eggers et al. |
| 5,861,003 A | 1/1999 | Latson et al. |
| 5,865,730 A | 2/1999 | Fox et al. |
| 5,865,791 A | 2/1999 | Whayne et al. |
| 5,871,017 A | 2/1999 | Mayer |
| 5,875,782 A | 3/1999 | Ferrari et al. |
| 5,876,325 A | 3/1999 | Mizuno et al. |
| 5,876,449 A | 3/1999 | Starck et al. |
| 5,879,366 A | 3/1999 | Shaw et al. |
| 5,882,340 A | 3/1999 | Yoon |
| 5,910,150 A | 6/1999 | Saadat |
| 5,916,145 A | 6/1999 | Chu et al. |
| 5,924,424 A | 7/1999 | Stevens et al. |
| 5,925,062 A | 7/1999 | Purdy |
| 5,925,076 A | 7/1999 | Inoue |
| 5,928,260 A | 7/1999 | Chin et al. |
| 5,961,440 A | 10/1999 | Schweich, Jr. et al. |
| 5,961,539 A | 10/1999 | Northrup, III et al. |
| 5,984,917 A | 11/1999 | Fleischman et al. |
| 6,024,096 A | 2/2000 | Buckberg |
| 6,024,756 A | 2/2000 | Huebsch et al. |
| 6,036,720 A | 3/2000 | Abrams et al. |
| 6,045,497 A | 4/2000 | Schweich, Jr. et al. |
| 6,059,715 A | 5/2000 | Schweich, Jr. et al. |
| 6,076,013 A | 6/2000 | Brennan et al. |
| 6,077,214 A | 6/2000 | Mortier et al. |
| 6,077,218 A | 6/2000 | Alferness |
| 6,093,199 A | 7/2000 | Brown et al. |
| 6,095,968 A | 8/2000 | Snyders |
| 6,096,347 A | 8/2000 | Geddes et al. |
| 6,099,832 A | 8/2000 | Mickle et al. |
| 6,102,887 A | 8/2000 | Altman |
| 6,125,852 A | 10/2000 | Stevens et al. |
| 6,132,438 A | 10/2000 | Fleischman et al. |
| 6,142,973 A | 11/2000 | Carleton et al. |
| 6,152,144 A | 11/2000 | Lesh et al. |
| 6,155,968 A | 12/2000 | Wilk |
| 6,156,027 A | 12/2000 | West |
| 6,161,543 A | 12/2000 | Cox et al. |
| 6,193,731 B1 | 2/2001 | Oppelt et al. |
| 6,221,092 B1 | 4/2001 | Koike et al. |
| 6,221,104 B1 | 4/2001 | Buckberg et al. |
| 6,230,714 B1 | 5/2001 | Alferness et al. |
| 6,231,561 B1 | 5/2001 | Frazier et al. |
| 6,258,021 B1 | 7/2001 | Wilk |
| 6,264,630 B1 | 7/2001 | Mickley et al. |
| 6,267,772 B1 | 7/2001 | Mulhauser et al. |
| 6,290,674 B1 | 9/2001 | Roue et al. |
| 6,296,656 B1 | 10/2001 | Bolduc et al. |
| 6,312,446 B1 | 11/2001 | Huebsch et al. |
| 6,328,727 B1 | 12/2001 | Frazier et al. |
| 6,334,864 B1 | 1/2002 | Amplatz et al. |
| 6,343,605 B1 | 2/2002 | Lafontaine |
| 6,348,068 B1 | 2/2002 | Campbell et al. |
| 6,355,052 B1 | 3/2002 | Neuss et al. |
| 6,360,749 B1 | 3/2002 | Jayaraman |
| 6,364,896 B1 | 4/2002 | Addis |
| 6,387,042 B1 | 5/2002 | Herrero |
| 6,406,420 B1 | 6/2002 | McCarthy et al. |
| 6,419,669 B1 | 7/2002 | Frazier et al. |
| 6,436,088 B2 | 8/2002 | Frazier et al. |
| 6,450,171 B1 | 9/2002 | Buckberg et al. |
| 6,482,146 B1 | 11/2002 | Alferness et al. |
| 6,482,228 B1 | 11/2002 | Norred |
| 6,506,204 B2 | 1/2003 | Mazzocchi |
| 6,508,756 B1 | 1/2003 | Kung et al. |
| 6,511,496 B1 | 1/2003 | Huter et al. |
| 6,537,198 B1 | 3/2003 | Vidlund et al. |
| 6,551,303 B1 | 4/2003 | Van Tassel et al. |
| 6,572,643 B1 | 6/2003 | Gharibadeh |
| 6,586,414 B2 | 7/2003 | Haque et al. |
| 6,592,608 B2 | 7/2003 | Fisher et al. |
| 6,613,013 B2 | 9/2003 | Haarala et al. |
| 6,622,730 B2 | 9/2003 | Ekvall et al. |
| 6,645,199 B1 | 11/2003 | Jenkins et al. |
| 6,652,555 B1 | 11/2003 | VanTassel et al. |
| 6,681,773 B2 | 1/2004 | Murphy et al. |
| 6,685,627 B2 | 2/2004 | Jayaraman |
| 6,702,763 B2 | 3/2004 | Murphy et al. |
| 6,730,108 B2 | 5/2004 | Van Tassel et al. |
| 6,776,754 B1 | 8/2004 | Wilk |
| 6,852,076 B2 | 2/2005 | Nikolic et al. |
| 6,887,192 B1 | 5/2005 | Whayne et al. |
| 6,951,534 B2 | 10/2005 | Girard et al. |

(56) References Cited

U.S. PATENT DOCUMENTS

| | | |
|---|---|---|
| 6,959,711 B2 | 11/2005 | Murphy et al. |
| 6,994,093 B2 | 2/2006 | Murphy et al. |
| 7,144,363 B2 | 12/2006 | Pai et al. |
| 7,172,551 B2 | 2/2007 | Leasure |
| 7,175,660 B2 | 2/2007 | Cartledge et al. |
| 7,279,007 B2 | 10/2007 | Nikolic et al. |
| 7,303,526 B2 | 12/2007 | Sharkey et al. |
| 7,320,665 B2 * | 1/2008 | Vijay ............... A61B 17/12122 600/16 |
| 7,399,271 B2 | 7/2008 | Khairkhahan et al. |
| 7,485,088 B2 | 2/2009 | Murphy et al. |
| 7,530,998 B1 | 5/2009 | Starkey |
| 7,569,062 B1 | 8/2009 | Kuehn et al. |
| 7,582,051 B2 | 9/2009 | Khairkhahan et al. |
| 7,674,222 B2 | 3/2010 | Nikolic et al. |
| 7,758,491 B2 | 7/2010 | Buckner et al. |
| 7,762,943 B2 | 7/2010 | Khairkhahan |
| 7,824,325 B2 | 11/2010 | Dubi |
| 7,862,500 B2 | 1/2011 | Khairkhahan et al. |
| 7,887,477 B2 | 2/2011 | Nikolic et al. |
| 7,897,086 B2 | 3/2011 | Khairkhahan et al. |
| 7,938,767 B2 | 5/2011 | Evans et al. |
| 7,976,455 B2 | 7/2011 | Khairkhahan |
| 7,993,258 B2 | 8/2011 | Feld et al. |
| 8,192,478 B2 | 6/2012 | Khairkhahan et al. |
| 8,246,671 B2 | 8/2012 | Khairkhahan |
| 8,257,428 B2 | 9/2012 | Khairkhahan et al. |
| 8,377,114 B2 | 2/2013 | Khairkhahan et al. |
| 8,382,653 B2 | 2/2013 | Dubi et al. |
| 8,388,672 B2 | 3/2013 | Khairkhahan et al. |
| 8,398,537 B2 | 3/2013 | Khairkhahan et al. |
| 8,500,622 B2 | 8/2013 | Lipperman et al. |
| 8,500,790 B2 | 8/2013 | Khairkhahan |
| 8,500,795 B2 | 8/2013 | Khairkhahan et al. |
| 8,529,430 B2 | 9/2013 | Nikolic et al. |
| 8,657,873 B2 | 2/2014 | Khairkhahan et al. |
| 8,672,827 B2 | 3/2014 | Nikolic et al. |
| 8,764,848 B2 | 7/2014 | Callaghan et al. |
| 8,790,242 B2 | 7/2014 | Kermode et al. |
| 8,827,892 B2 | 9/2014 | Nikolic et al. |
| 8,931,159 B2 | 1/2015 | Hillukka |
| 9,017,394 B2 | 4/2015 | Khairkhahan |
| 9,039,597 B2 | 5/2015 | Kermode et al. |
| 9,078,660 B2 | 7/2015 | Boutillette et al. |
| 9,192,496 B2 | 11/2015 | Robinson |
| 9,332,992 B2 | 5/2016 | Alexander |
| 9,332,993 B2 | 5/2016 | Kermode et al. |
| 9,364,327 B2 | 6/2016 | Kermode et al. |
| 9,592,123 B2 | 3/2017 | Nikolic et al. |
| 10,251,750 B2 * | 4/2019 | Alexander ....... A61B 17/12022 |
| 10,307,147 B2 | 6/2019 | Khairkhahan et al. |
| 2001/0014800 A1 | 8/2001 | Frazier et al. |
| 2002/0019580 A1 | 2/2002 | Lau et al. |
| 2002/0026092 A1 | 2/2002 | Buckberg et al. |
| 2002/0028981 A1 | 3/2002 | Lau et al. |
| 2002/0032481 A1 | 3/2002 | Gabbay |
| 2002/0055767 A1 | 5/2002 | Forde et al. |
| 2002/0055775 A1 | 5/2002 | Carpentier et al. |
| 2002/0056461 A1 | 5/2002 | Jayaraman |
| 2002/0111647 A1 | 8/2002 | Khairkhahan et al. |
| 2002/0133227 A1 | 9/2002 | Murphy et al. |
| 2002/0161392 A1 | 10/2002 | Dubrul |
| 2002/0161394 A1 | 10/2002 | Macoviak et al. |
| 2002/0169359 A1 | 11/2002 | McCarthy et al. |
| 2002/0169360 A1 | 11/2002 | Taylor et al. |
| 2002/0183604 A1 | 12/2002 | Gowda et al. |
| 2002/0183827 A1 | 12/2002 | Derus et al. |
| 2002/0188170 A1 | 12/2002 | Santamore et al. |
| 2003/0012337 A1 | 1/2003 | Fewster et al. |
| 2003/0045896 A1 | 3/2003 | Murphy et al. |
| 2003/0050682 A1 | 3/2003 | Sharkey et al. |
| 2003/0050685 A1 | 3/2003 | Nikolic et al. |
| 2003/0057156 A1 | 3/2003 | Peterson et al. |
| 2003/0078671 A1 | 4/2003 | Lesniak et al. |
| 2003/0105384 A1 | 6/2003 | Sharkey et al. |
| 2003/0109770 A1 | 6/2003 | Sharkey et al. |
| 2003/0120337 A1 | 6/2003 | Van Tassel et al. |
| 2003/0135230 A1 | 7/2003 | Massey et al. |
| 2003/0149333 A1 | 8/2003 | Alferness |
| 2003/0149422 A1 | 8/2003 | Muller |
| 2003/0158570 A1 | 8/2003 | Ferrazzi |
| 2003/0181928 A1 | 9/2003 | Vidlund et al. |
| 2003/0181942 A1 | 9/2003 | Sutton et al. |
| 2003/0212429 A1 | 11/2003 | Keegan et al. |
| 2003/0220667 A1 | 11/2003 | van der Burg et al. |
| 2003/0225445 A1 | 12/2003 | Derus et al. |
| 2003/0229265 A1 | 12/2003 | Girard et al. |
| 2004/0002626 A1 | 1/2004 | Feld et al. |
| 2004/0034366 A1 | 2/2004 | van der Burg et al. |
| 2004/0044361 A1 | 3/2004 | Frazier et al. |
| 2004/0049210 A1 | 3/2004 | VanTassel et al. |
| 2004/0054394 A1 | 3/2004 | Lee |
| 2004/0064014 A1 | 4/2004 | Melvin et al. |
| 2004/0122090 A1 | 6/2004 | Lipton |
| 2004/0127935 A1 | 7/2004 | VanTassel et al. |
| 2004/0133062 A1 | 7/2004 | Pai et al. |
| 2004/0136992 A1 | 7/2004 | Burton et al. |
| 2004/0172042 A1 | 9/2004 | Suon et al. |
| 2004/0186511 A1 | 9/2004 | Stephens et al. |
| 2004/0215230 A1 | 10/2004 | Frazier et al. |
| 2004/0220610 A1 | 11/2004 | Kreidler et al. |
| 2004/0243170 A1 | 12/2004 | Suresh et al. |
| 2004/0260331 A1 | 12/2004 | D'Aquanni et al. |
| 2004/0260346 A1 | 12/2004 | Overall et al. |
| 2004/0267086 A1 | 12/2004 | Anstadt et al. |
| 2004/0267378 A1 | 12/2004 | Gazi et al. |
| 2005/0007031 A1 | 1/2005 | Hyder |
| 2005/0015109 A1 | 1/2005 | Lichtenstein |
| 2005/0038470 A1 | 2/2005 | van der Burg et al. |
| 2005/0043708 A1 | 2/2005 | Gleeson et al. |
| 2005/0065548 A1 | 3/2005 | Marino et al. |
| 2005/0085826 A1 | 4/2005 | Nair et al. |
| 2005/0096498 A1 | 5/2005 | Houser et al. |
| 2005/0113811 A1 | 5/2005 | Houser et al. |
| 2005/0113861 A1 | 5/2005 | Corcoran et al. |
| 2005/0124849 A1 | 6/2005 | Barbut et al. |
| 2005/0137690 A1 | 6/2005 | Salahieh et al. |
| 2005/0142180 A1 | 6/2005 | Bisgaier et al. |
| 2005/0154252 A1 | 7/2005 | Sharkey et al. |
| 2005/0177180 A1 | 8/2005 | Kaganov et al. |
| 2005/0187620 A1 | 8/2005 | Pai et al. |
| 2005/0197716 A1 | 9/2005 | Sharkey et al. |
| 2005/0216052 A1 | 9/2005 | Mazzocchi et al. |
| 2005/0228434 A1 | 10/2005 | Amplatz et al. |
| 2005/0256532 A1 | 11/2005 | Nayak et al. |
| 2005/0277981 A1 | 12/2005 | Maahs et al. |
| 2005/0277983 A1 | 12/2005 | Saadat et al. |
| 2005/0283218 A1 | 12/2005 | Williams |
| 2006/0014998 A1 | 1/2006 | Sharkey et al. |
| 2006/0019888 A1 | 1/2006 | Zhou |
| 2006/0025800 A1 | 2/2006 | Suresh |
| 2006/0030881 A1 | 2/2006 | Sharkey et al. |
| 2006/0063970 A1 | 3/2006 | Raman et al. |
| 2006/0069430 A9 | 3/2006 | Rahdert et al. |
| 2006/0079736 A1 | 4/2006 | Chin et al. |
| 2006/0116692 A1 | 6/2006 | Ward |
| 2006/0135947 A1 | 6/2006 | Soltesz et al. |
| 2006/0136043 A1 | 6/2006 | Cully et al. |
| 2006/0167334 A1 | 7/2006 | Anstadt et al. |
| 2006/0173524 A1 | 8/2006 | Salahieh et al. |
| 2006/0199995 A1 * | 9/2006 | Vijay ............... A61B 17/12122 600/16 |
| 2006/0229491 A1 | 10/2006 | Sharkey et al. |
| 2006/0241334 A1 | 10/2006 | Dubi et al. |
| 2006/0259124 A1 | 11/2006 | Matsuoka et al. |
| 2006/0264980 A1 | 11/2006 | Khairkhahan et al. |
| 2006/0276684 A1 | 12/2006 | Speziali |
| 2006/0281965 A1 | 12/2006 | Khairkhahan et al. |
| 2007/0129753 A1 | 6/2007 | Quinn et al. |
| 2007/0135826 A1 | 6/2007 | Zaver et al. |
| 2007/0135889 A1 | 6/2007 | Moore et al. |
| 2007/0161846 A1 | 7/2007 | Nikolic et al. |
| 2007/0162048 A1 | 7/2007 | Quinn et al. |
| 2007/0213578 A1 | 9/2007 | Khairkhahan et al. |

(56) References Cited

U.S. PATENT DOCUMENTS

| | | |
|---|---|---|
| 2007/0213815 A1 | 9/2007 | Khairkhahan et al. |
| 2007/0270931 A1 | 11/2007 | Leanna et al. |
| 2008/0015717 A1 | 1/2008 | Griffin et al. |
| 2008/0045778 A1 | 2/2008 | Lichtenstein et al. |
| 2008/0071133 A1 | 3/2008 | Dubi |
| 2008/0071134 A1 | 3/2008 | Dubi et al. |
| 2008/0221384 A1 | 9/2008 | Chi Sing et al. |
| 2008/0228205 A1 | 9/2008 | Sharkey et al. |
| 2008/0293996 A1 | 11/2008 | Evans et al. |
| 2008/0300672 A1 | 12/2008 | Kassab et al. |
| 2008/0319254 A1 | 12/2008 | Nikolic et al. |
| 2009/0054723 A1 | 2/2009 | Khairkhahan et al. |
| 2009/0062601 A1 | 3/2009 | Khairkhahan et al. |
| 2009/0112050 A1 | 4/2009 | Farnan et al. |
| 2009/0187063 A1 | 7/2009 | Khairkhahan |
| 2009/0228093 A1 | 9/2009 | Taylor et al. |
| 2009/0287040 A1* | 11/2009 | Khairkhahan ... A61B 17/12022 600/37 |
| 2010/0022821 A1 | 1/2010 | Dubi et al. |
| 2010/0030256 A1 | 2/2010 | Dubrul et al. |
| 2010/0057185 A1 | 3/2010 | Melsheimer et al. |
| 2010/0121132 A1 | 5/2010 | Nikolic et al. |
| 2010/0274227 A1 | 10/2010 | Khairkhahan et al. |
| 2011/0021864 A1 | 1/2011 | Criscione et al. |
| 2011/0046712 A1 | 2/2011 | Melsheimer et al. |
| 2011/0087066 A1* | 4/2011 | Boutillette ...... A61B 17/12172 600/37 |
| 2011/0092761 A1 | 4/2011 | Almog et al. |
| 2011/0098525 A1 | 4/2011 | Kermode et al. |
| 2011/0178362 A1 | 7/2011 | Evans et al. |
| 2011/0257461 A1 | 10/2011 | Lipperman et al. |
| 2011/0264204 A1 | 10/2011 | Khairkhahan |
| 2012/0041257 A1 | 2/2012 | Stankus et al. |
| 2012/0245604 A1 | 9/2012 | Tegzes |
| 2012/0330408 A1 | 12/2012 | Hillukka et al. |
| 2013/0090677 A1 | 4/2013 | Evans et al. |
| 2013/0165735 A1 | 6/2013 | Khairkhahan et al. |
| 2013/0274595 A1 | 10/2013 | Kermode et al. |
| 2014/0180271 A1 | 6/2014 | Johnson et al. |
| 2014/0296624 A1 | 10/2014 | Kermode et al. |
| 2014/0343356 A1 | 11/2014 | Nikolic et al. |
| 2014/0345109 A1 | 11/2014 | Grant et al. |
| 2014/0364941 A1 | 12/2014 | Edmiston et al. |
| 2014/0371789 A1 | 12/2014 | Hariton et al. |
| 2015/0209144 A1 | 7/2015 | Khairkhahan |
| 2015/0265405 A1 | 9/2015 | Boutillette et al. |
| 2015/0297381 A1 | 10/2015 | Essinger et al. |
| 2016/0184094 A1* | 6/2016 | Iobbi .................. A61F 2/243 623/2.11 |
| 2016/0262892 A1 | 9/2016 | Kermode et al. |

FOREIGN PATENT DOCUMENTS

| | | |
|---|---|---|
| EP | 2082690 B1 | 6/2012 |
| WO | 9803213 A1 | 1/1998 |
| WO | 0245710 A1 | 6/2002 |
| WO | 02087481 A1 | 11/2002 |
| WO | 03103743 A2 | 12/2003 |
| WO | 2004012629 A1 | 2/2004 |
| WO | 2008010792 A1 | 1/2008 |
| WO | 2011041422 A2 | 4/2011 |
| WO | 2012099418 A2 | 7/2012 |
| WO | 2013065036 A2 | 5/2013 |
| WO | 2013128461 A1 | 9/2013 |
| WO | 2014141209 A1 | 9/2014 |
| WO | WO-2014152461 A2 * | 9/2014 ....... A61B 17/12122 |

OTHER PUBLICATIONS

Anand et al.; Isolated myocyte contractile function is normal in postinfarct remodeled rat heart with systolic dysfunction; Circulation; 96(11); pp. 3974-3984; Dec. 1997.

Boersma et al.; Early thrombolytic treatment in acute myocardial infarction: reappraisal of the golden hour; Lancet: vol. 348(9030); pp. 771-775; Sep. 21, 1996.

Bozdag-Turan et al.; Left ventricular partitioning device in a patient with chronic heart failure: Short-term clinical follow-up; Int J Cardiol; 163(1); pp. e1-e3; (Epub) Jul. 2012.

Dang et al.; Akinetic myocardial infarcts must contain contracting myocytes: finite-element model study; Am J Physiol Heart Circ Physiol ; 288; pp. H1844-H1850; Apr. 2005.

Dang et al.; Effect of ventricular size and patch stiffness in surgical anterior ventricular restoration: a finite element model study; Ann Thorac Surg; 79; pp. 185-193; Jan. 2005.

Di Mattia et al. Surgical treatment of left ventricular post-infarction aneurysm with endoventriculoplasty: late clinical and functioal results. European Journal of Cardio-thoracic Surgery. 15(4):413-418; Apr. 1999.

Dor et al. Ventricular remodeling in coronary artery disease. Current Opinion in Cardiology. 12(6):533-537; Nov. 1997.

Dor V. The treatment of refractory ischemic ventricular tachycardia by endoventricular patch plasty reconstruction of the left ventricle. Seminars in Thoracic and Cardiovascular Surgery. 9(2): 146-155; Apr. 1997.

Dor. Surgery for left ventricular aneurysm. Current Opinion in Cardiology. vol. 5; No. 6; pp. 773-780; Dec. 1990.

Gore Medical. www.goremedical.com. "Helex Septal Occluder" product description. Accessed Apr. 3, 2002.

Grossman et al.; Wall stress and patterns of hypertrophy in the human left ventricle; J Clin Invest; 56; pp. 56-64; Jul. 1975.

Guccione et al.; Finite element stress analysis of left ventricular mechanics in the beating dog heart; J Biomech; 28; pp. 1167-1177; Oct. 1995.

Guccione et al.; Mechanics of active contraction in cardiac muscle: Part II—Cylindrical models of the systolic left ventricle; J Biomech Eng; 115; pp. 82-90; Feb. 1993.

Gutberlet et al.; Myocardial viability assessment in patients with highly impaired left ventricular function: comparison of delayed enhancement dobutamine stress MRI end-diastolic wall thickness and TI201-SPECT with functional recovery after revascularization; Eur Radiol; 15; pp. 872-880; May 2005.

Huisman et al.; Measurement of left ventricular wall stress; Cardiovascular Research; 14; pp. 142-153; Mar. 1980.

James et al.; Blood Volume and Brain Natriuretic Peptide in Congestive Heart Failure: A Pilot Study; American Heart Journal; vol. 150; issue 5 pp. 984.e1-984.e6 (abstract); Dec. 6, 2005.

Januzzi James L.; Natriuretic peptide testing: A window into the diagnosis and prognosis of heart failure; Cleveland Clinic Journal of Medicine; vol. 73; No. 2; pp. 149-152 and 155-157; Feb. 2006.

Jones et al.; Coronary Bypass Surgery with or without Surgical Ventricular Reconstruction; N Engl J Med; 360; pp. 1705-1717; Apr. 2009.

Kawata et al. Systolic and Diastolic Function after Patch Reconstruction of Left Ventricular Aneurysms. Ann. Thorac. Surg. 5(2)9:403-407; Feb. 1995.

Lee et al.; A novel method for quantifying in-vivo regional left ventricular myocardial contractility in the border zone of a myocardial infarction (author manuscript 11 pgs.); J Biomech Eng; 133; 094506; Sep. 2011.

Mazzaferri et al.; Percutaneous left ventricular partitioning in patients with chronic heart failure and a prior anterior myocardial infarction: Results of the Percutaneous Ventricular Restoration in Chronic Heart Failure Patients Trial; Am Heart J; 163; pp. 812-820; May 2012.

Nikolic et al.; Percutaneous implantation of an intraventricular device for the treatment of heart failure: experimental results and proof of concept; J Card Fail; 15(9); pp. 790-797; Nov. 2009.

Priola et al.; Functional characteristics of the left ventricular inflow and outflow tracts; Circ Res; 17; pp. 123-129; Aug. 1965.

Sagic et al.; Percutaneous implantation of the left ventricular partitioning device for chronic heart failure: a pilot study with 1-year follow-up. Eur J Heart Fail; 12; pp. 600-606; Apr. 2010.

Sun et al.; A computationally efficient formal optimization of regional myocardial contractility in a sheep with left ventricular aneurysm (author manuscript 21 pgs.); J Biomech Eng; 131; 111001; Nov. 2009.

(56) References Cited

OTHER PUBLICATIONS

U.S. Food & Drug Administration; AneuRx Stent Graft System—Instructions for use; (pre-market approval); Sep. 29, 1999; downloaded Apr. 25, 2013 (http:www.accessdata.fda.govcdrh_docspdfP990020c.pdf).

Walker et al; Magnetic resonance imaging-based finite element stress analysis after linear repair of left ventricular aneurysm (author manuscript 17 pgs.); J Thorac Cardiovasc Surg; 135; pp. 1094-1102 e1-2; May 2008.

Walker et al; MRI-based finite-element analysis of left ventricular aneurysm; Am J Physiol Heart Circ Physiol; 289; pp. H692-H700; Aug. 2005.

Walmsley; Anatomy of left ventricular outflow tract; British Heart Journal; 41; pp. 263-267; Mar. 1979.

Wenk et al.; First evidence of depressed contractility in the border zone of a human myocardial infarction; Ann Thorac Surg; 93; pp. 1188-1193; Apr. 2012.

Wenk et al.; Regional left ventricular myocardial contractility and stress in a finite element model of posterobasal myocardial infarction (author manuscript pgs.); J Biomech Eng; 133(4); 044501; Apr. 2011.

\* cited by examiner

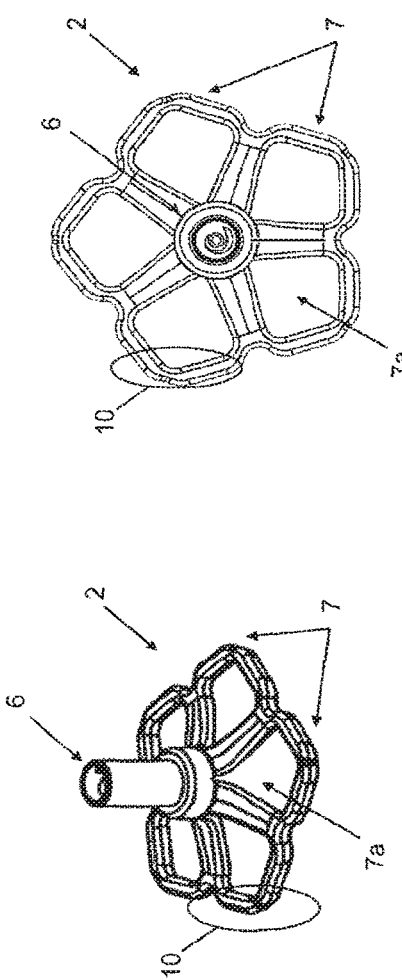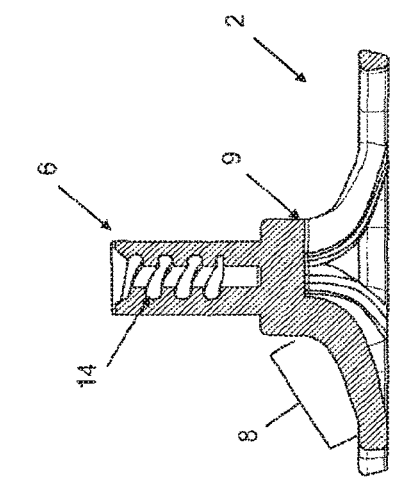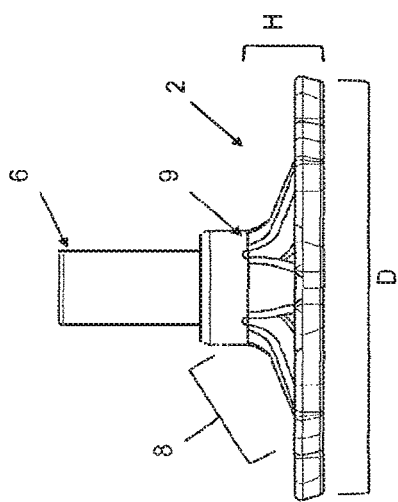

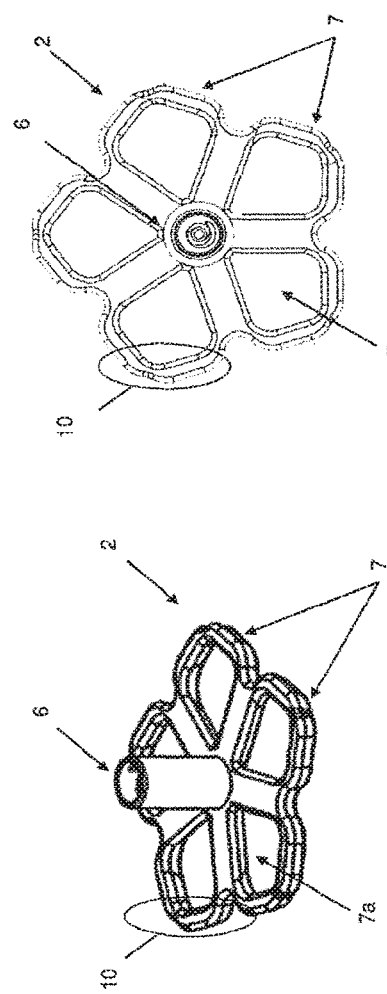
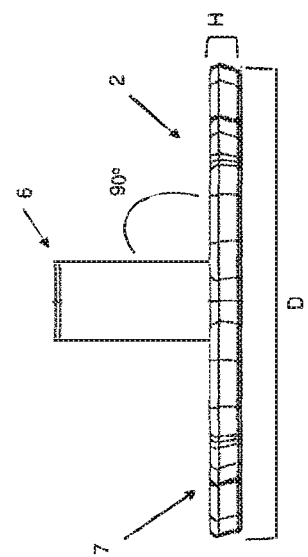

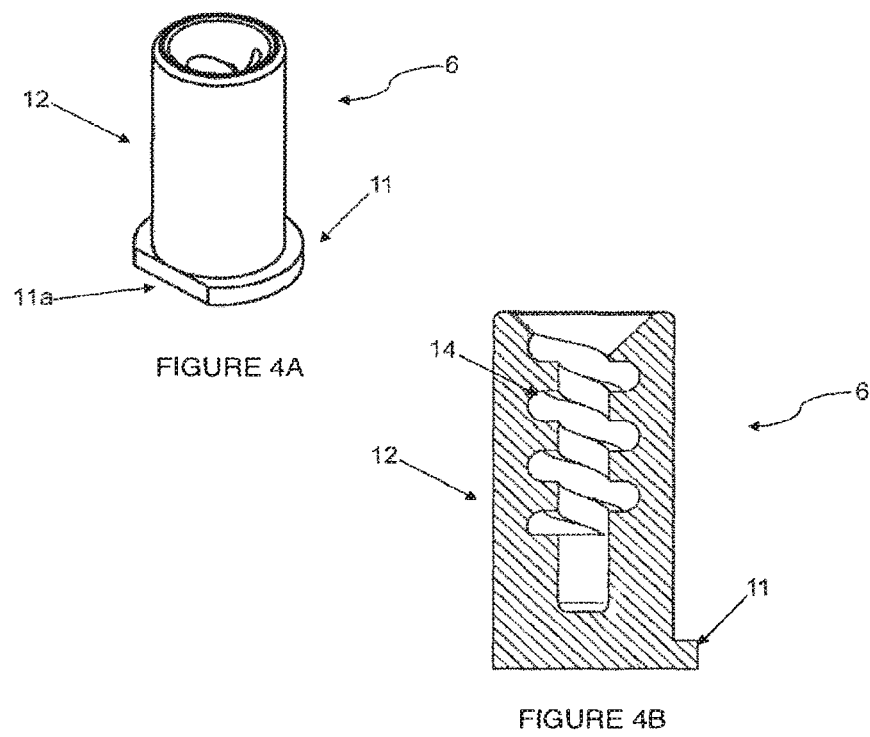
FIGURE 4A
FIGURE 4B
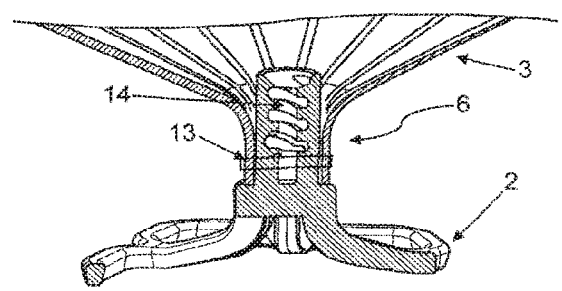
FIGURE 4C

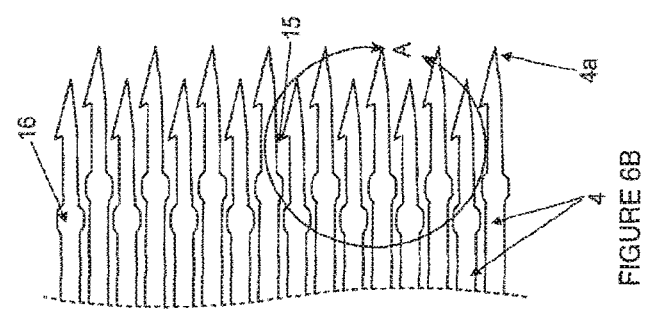
FIGURE 6A
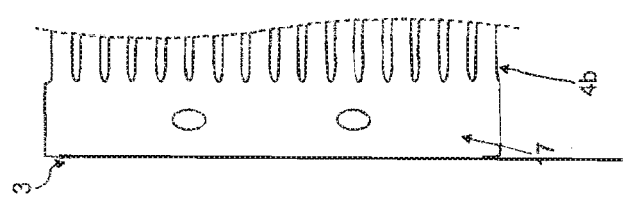
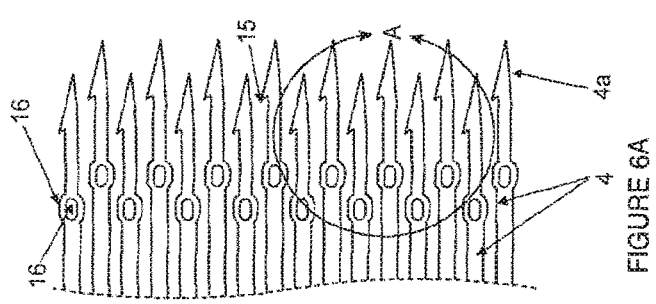
FIGURE 6B
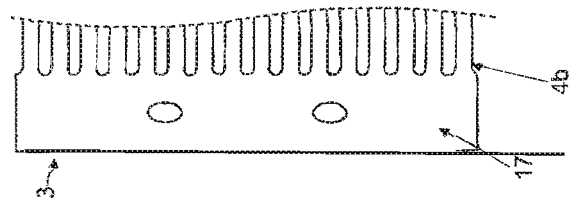
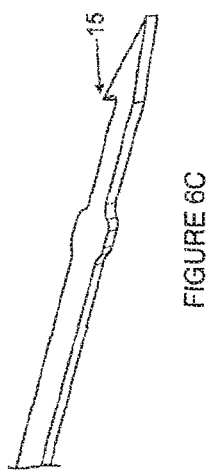
FIGURE 6C

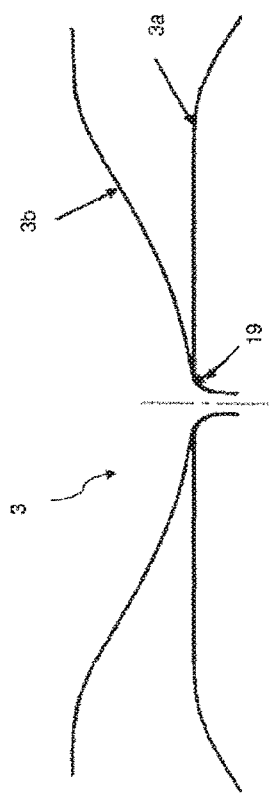
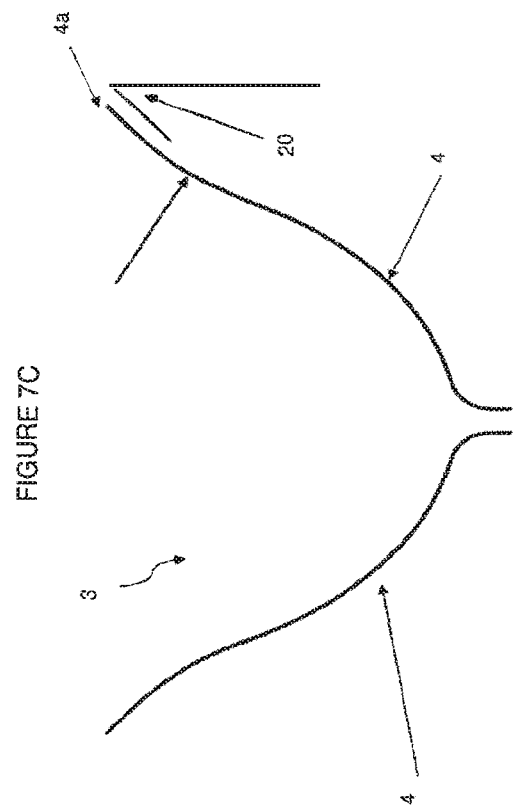

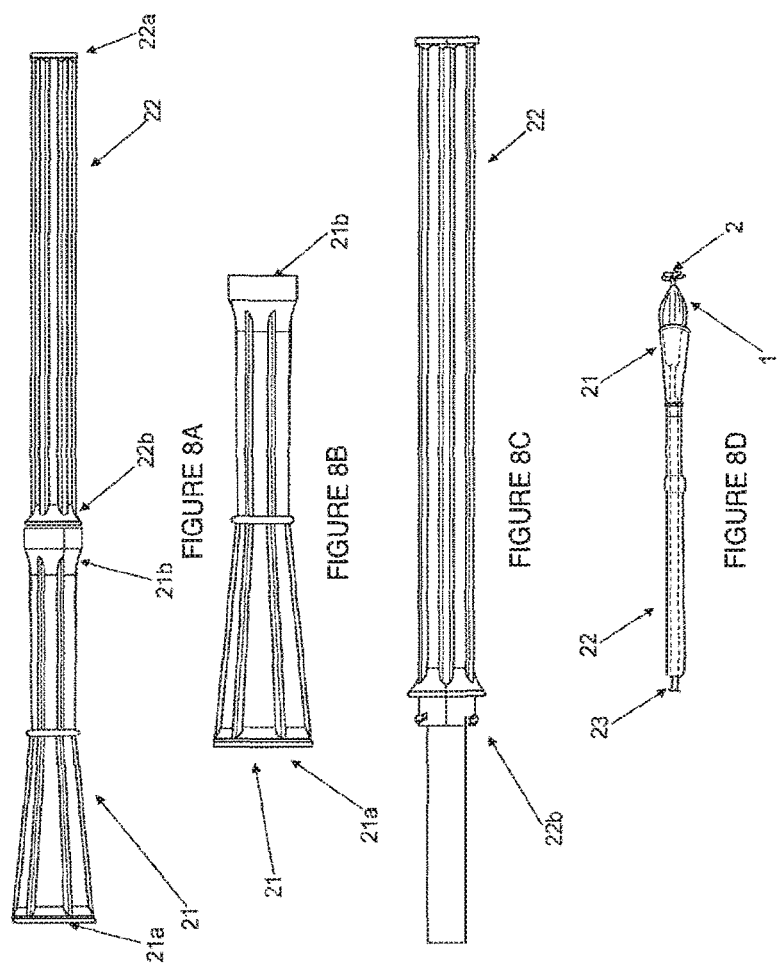

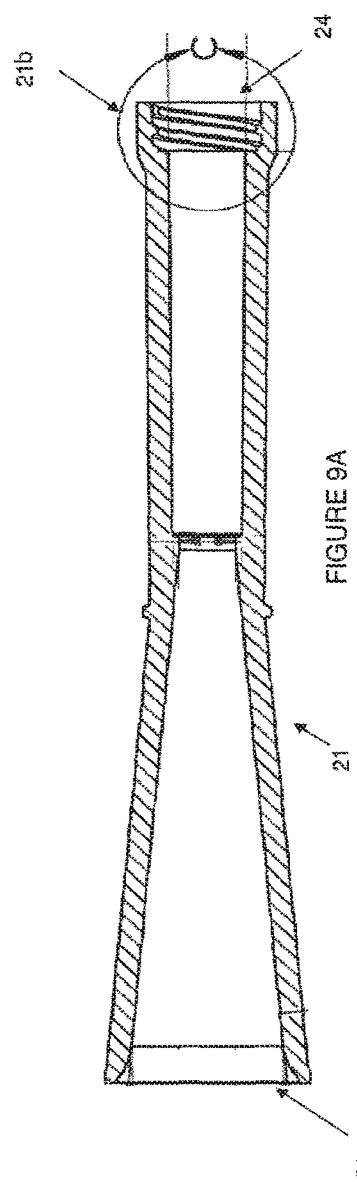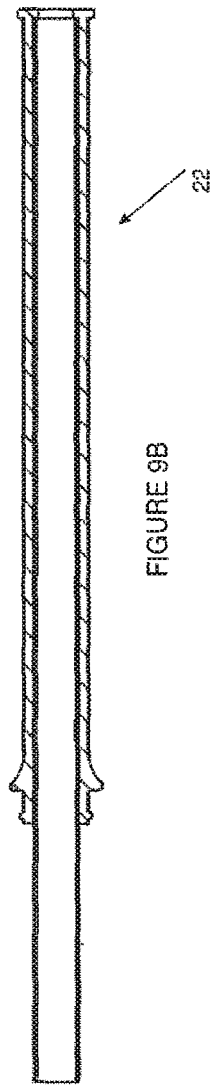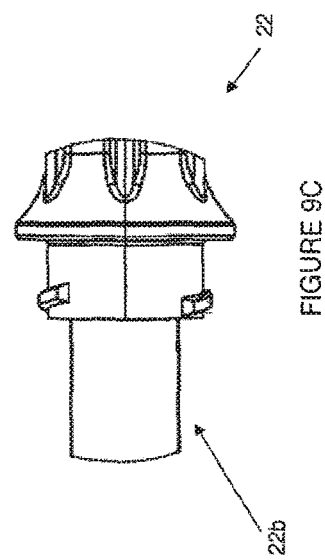
FIGURE 9A
FIGURE 9B
FIGURE 9C

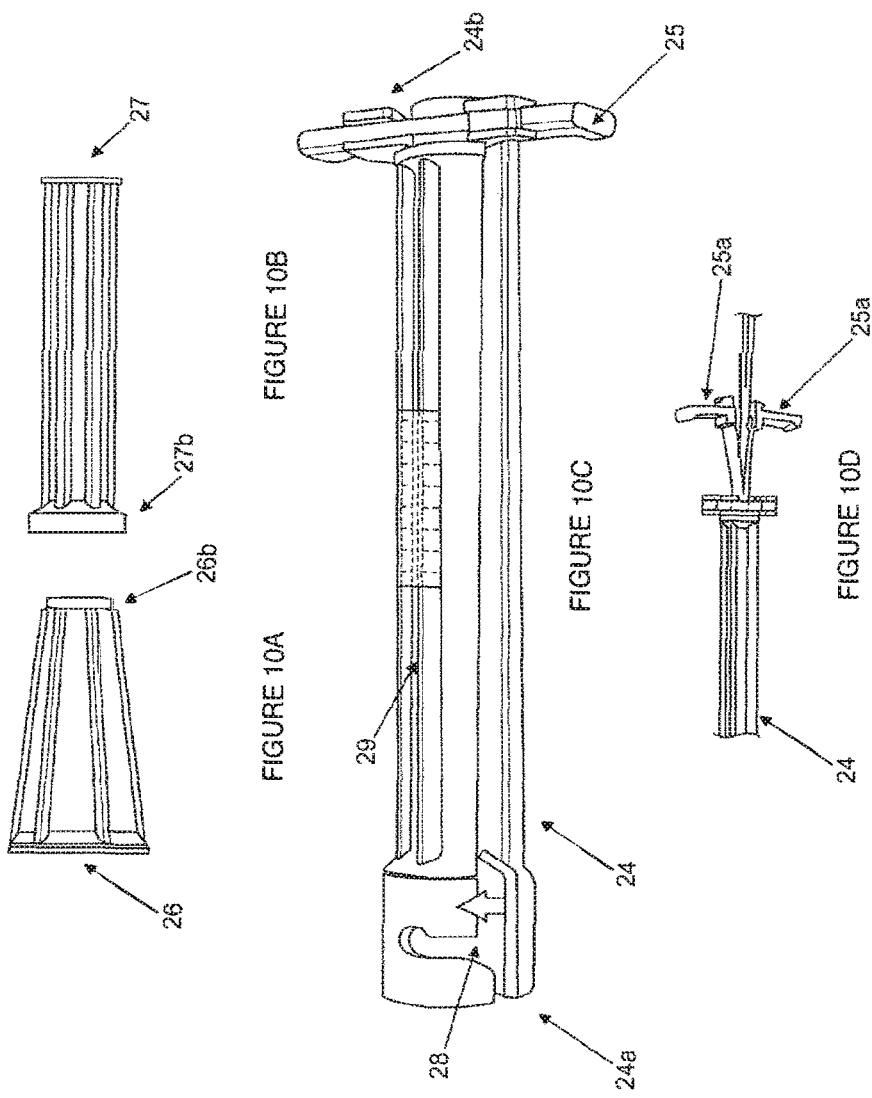

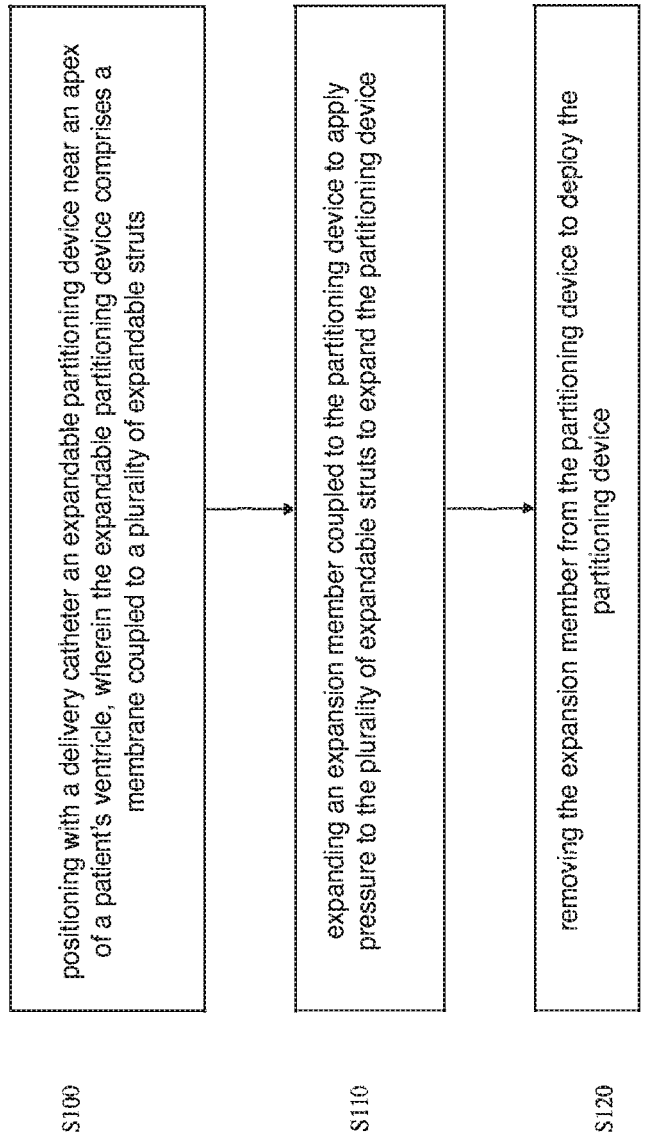

SYSTEMS AND METHODS FOR TREATING CARDIAC DYSFUNCTION

CROSS REFERENCE TO RELATED APPLICATIONS

This application is a continuation of U.S. patent application Ser. No. 15/506,562, filed Feb. 24, 2017, now U.S. Pat. No. 10,751,183 which claims priority to International Patent Application No. PCT/US2015/050827, filed Sep. 18, 2015, which claims priority to Chinese utility model patent application no. 201420564242.9, filed on Sep. 28, 2014 (titled "IMPLANT LOADING SYSTEMS"), which issued on Mar. 4, 2015 as ZL201420564242.9; Chinese utility model patent application no. 201420564809.2, filed on Sep. 28, 2014 (titled "EXPANDABLE DEVICES FOR INSERTING INTO A VENTRICLE OF A HEART TO TREAT HEART FAILURE"), which issued on Mar. 11, 2015 as ZL 2014205648092; and Chinese utility model patent application no. 201420564806.9, filed on Sep. 28, 2014 (titled "SYSTEMS OF EXPANDABLE DEVICES AND DELIVERY CATHETERS FOR TREATING CARDIAC DYSFUNCTION"), which issued on Feb. 25, 2015 as ZL 201420564806.9. Each of these applications is herein incorporated by reference in its entirety.

TECHNICAL FIELD

Described herein are ventricular devices useful for treating cardiac dysfunction.

BACKGROUND

Congestive heart failure (CHF) is a chronic medical condition in which the heart progressively enlarges. The enlarged heart cannot deliver sufficient oxygenated and nutrient rich blood to the body's cells. CHF is commonly associated with left ventricular dysfunction and/or diastolic dysfunction. Left ventricular dysfunction results from impaired emptying of the left ventricular heart chamber. In contrast, diastolic dysfunction refers to alterations in left ventricular properties that adversely affect ventricular filling and diastolic pressure.

A key aspect of normal diastolic filling is the contribution of left ventricular elastic recoil forces to left ventricular filling. Elastic recoil is the ability of the stretched heart to return to its resting position. For example, in a healthy heart, the end-diastolic dimension of the left ventricle may range from 36-56 mm (relaxed) and the end-systolic dimension of the left ventricle may range from 20-40 mm (contracted). A left ventricle in heart failure would typically have larger dimensions than those of a healthy heart. Elastic recoil forces are important in early diastole because they allow rapid and enhanced early filling by assisting the expansion of the left ventricle.

In the case of heart enlargement and/or a decrease in myocardial function, elastic recoil forces may be reduced or absent, thus ceasing to assist early ventricular filling and leading to an increase of the ventricular filling pressure. For example, a patient experiencing CHF typically has an ejection fraction of 40% or less.

Thus, there is a need for a new and useful system, device, and method for treating cardiac dysfunction. This new and useful apparatuses (e.g., systems, devices, and assemblies) and methods described herein may address these needs.

SUMMARY

Described herein are devices and systems for treating a cardiac dysfunction. In general, the devices and systems described herein may include improved expandable implant devices that can be collapsed for insertion into a ventricle of a human heart, and then expanded when in the heart. In general, the implants described herein am improved over earlier generations of implants because they may be used more safely and reliably. In particular, such devices may include a support frame having a plurality of expandable struts, to which a membrane is attached, where the struts am configured for cyclical loading. The struts of the support frame may have a roughness average of less than 1 µm. These expandable implants may also include a foot configured for contacting a first interior wall portion of the ventricle, wherein the first free ends of the struts extend beyond a diameter of the foot. The foot may have a durometer of between about 70 A to 90 A.

For example, an expandable device for inserting into a ventricle of a heart to treat heart failure may be characterized in that the device has: a support frame comprising a plurality of radially expandable struts, wherein each strut has a first free end and a second end, and wherein the struts are configured for cyclical loading; a foot configured for contacting a first interior wall portion of the ventricle, wherein the first free ends of the struts extend beyond a diameter of the foot; and a membrane coupled to the support frame.

Each of the first ends of the plurality of struts may comprise an anchor for engaging a second interior wall portion of a heart. The anchors may be staggered. Each strut may include a stop proximate the anchor, the stop may be adapted to keep the membrane in place on the support frame while also being adapted to reduce or prevent over-penetration of the strut into the second interior wall portion of the heart. The stop may include an eyelet.

The struts are adapted for cyclic loading. Cyclic loading means that the struts are configured to move (e.g. flex or bend) as the heart, and particularly the ventricle, beats. In addition, the membrane attached to the struts may push against blood flowing in the ventricle, and assist in ejecting blood from the ventricle. Repeated cyclic loading may weaken struts over time, which is particularly critical when the device is implanted into a heart. Thus, the struts described herein may be shaped with a curve and/or varying thickness, particularly in regions prone to stress fractures. For example, the struts may have a thickness that varies along the length of the struts. This is illustrated in greater detail below.

The support frame generally has a collapsed delivery configuration and an expanded deployed configuration.

The second ends of the plurality of struts may be flared, such that the width of the second ends is greater than the width of the first ends. A slot region may be disposed between two struts (e.g., between adjacent struts).

The support frame may have a roughness average of less than 1 µm.

In general, the foot may comprise a radiopaque material. The foot may be compressible or bendable. The foot may have a durometer between about 70 A to 90 A. The foot may have a height between about 0.5 mm to 4.0 mm.

For example, an expandable device for inserting into a ventricle of a heart to treat heart failure may be characterized in that the device has: a foot configured for contacting a first interior wall portion of a heart, wherein the foot has a durometer between about 70 A to 90 A; a support frame comprising a plurality of radially expandable struts configured for cyclical loading, wherein each strut has a first free end and a second end configured to extend beyond the foot; and a membrane coupled to the support frame, wherein each strut includes a stop proximate the free end, the stop adapted to keep the membrane in place on the support frame while also being adapted to reduce or prevent over-penetration of the strut into the second interior wall portion of the heart.

Also described herein are systems including both an expandable device, including any of the improved expandable devices described above, and a delivery catheter.

For example, a system including an expandable device for inserting into a heart ventricle to treat heart failure and a delivery catheter for deploying the expandable device into the ventricle may be characterized (improved from other such systems) in that the system includes: the expandable device comprising: a foot for contacting a first interior wall portion of a heart; a support frame comprising a plurality of radially expandable struts, wherein each strut has a first free end and a second end coupled to the foot; and a membrane coupled to the support frame; and the delivery catheter having: a proximal end and a distal end; an expansion member near the distal end of the delivery catheter configured to apply pressure to the support frame of the ventricular partitioning device to move the ventricular partitioning device from a collapsed delivery configuration to an expanded deployed configuration; and a coupling element configured to secure the expansion member to the ventricular partitioning device during deployment.

In general the expandable device (which may also be referred to as a ventricular partitioning device herein) may be configured to be loaded into a guide catheter using a funnel coupleable to a sleeve, as described in greater detail below. The system first ends of the plurality of struts may comprise an anchor for engaging a second interior wall portion of a heart. The anchors on the first ends of the plurality of struts may be configured to penetrate the second interior wall portion of the heart upon expanding the ventricular partitioning device. The coupling element may comprise a helical screw.

As mentioned above, the support frame may have a roughness average of less than 1 μm, and the foot may have a durometer between about 70 A to 90 A.

Any of these systems may also include a funnel with a flared first end and a second end, wherein the flared first end is configured for receiving the expandable device. Any of the funnels may include a sleeve removably coupled to the second end of the funnel, wherein the sleeve is configured to transfer the expandable device to a guide catheter.

For example, a system may include including an expandable device for inserting into a heart ventricle to treat heart failure and a delivery catheter for deploying the expandable device into the ventricle, characterized in that the system comprises: the expandable device having: a foot for contacting a first interior wall portion of a heart having a durometer between about 70 A to 90 A; a support frame having a roughness average of less than 1 μm, the support frame comprising a plurality of radially expandable struts, wherein each strut has a first free end and a second end coupled to the foot; and a membrane coupled to the support frame; the delivery catheter having: a proximal end and a distal end; an expansion member near the distal end of the delivery catheter configured to apply pressure to the support frame of the expandable device to move the expandable device from a collapsed delivery configuration to an expanded deployed configuration; and a coupling element configured to secure the expansion member to the expandable device during deployment.

Also described herein are systems or devices for loading the implant (expandable devices) described above. These device or systems may include a funnel and a releasably coupled sleeve. An implant may be coupled with the funnel and sleeve, for transferring to a delivery catheter.

For example, described herein are implant loading systems including a funnel for loading an expandable implant into a guide catheter for delivery to a ventricle to treat heart failure, characterized in that the implant loading system comprises: the funnel having: a flared first end and a second end, wherein the flared first end is configured for receiving and collapsing expandable implant; and a sleeve removably coupled to the second end of the funnel, wherein the sleeve is configured to transfer the expandable implant to a guide catheter.

The funnel may include a first portion at the first end and a second portion at the second end, the first portion comprising a tapering receptacle for receiving the expandable implant, and the second portion comprising a lumen having a first diameter.

The sleeve may include a lumen with a second diameter, wherein the first diameter is greater than the second diameter. The sleeve may also include a coupling element located in a center portion of the sleeve.

The sleeve may comprise a tubular portion distal to the coupling element, the tubular portion may be configured to be inserted into the second portion of the funnel. The tubular portion of the sleeve may have a length that is about equal to the length of the lumen of the second portion of the funnel.

In general, any of the implants described herein may be used with the implant loading devices and systems. For example, an expandable implant that may be used (or included with) these systems and devices may comprise: a foot; a support frame comprising a plurality of radially expandable struts, wherein each strut has a first free end and a second end coupled to the foot; and a membrane coupled to the support frame.

The flared first end of the funnel may be configured for receiving the first free end of the plurality of radially expandable struts. The implant loading system may be coupled to the expandable implant.

For example, an implant loading system including a funnel for loading an expandable implant into a guide catheter for delivery to a ventricle to treat heart failure, characterized in that the implant loading system comprises: the funnel having: a flared first end and a second end, wherein the flared first end comprises a tapering receptacle for receiving and collapsing the expandable implant, and a second portion at the second end comprising a lumen having a first diameter; and a sleeve removably coupled to the second end of the funnel, wherein the sleeve is configured to transfer the expandable implant to a guide catheter; a coupling element located in a center portion of the sleeve; and a tubular portion distal to the coupling element, the tubular portion configured to be inserted into the second portion of the funnel.

BRIEF DESCRIPTION OF THE DRAWINGS

FIGS. 2A-2D illustrate a foot of a ventricular partitioning device in accordance with a preferred embodiment;

FIGS. 3A-3C illustrate a foot of a ventricular partitioning device in accordance with an alternative preferred embodiment;

FIGS. 4A-4C illustrate a stem for coupling a membrane to a foot of a ventricular partitioning device, in accordance with a preferred embodiment;

FIGS. 6A-6C illustrate two embodiments of the struts of a ventricular partitioning device;

FIGS. 7A-7D illustrate a support frame, in accordance with a preferred embodiment;

FIGS. 8A-8D illustrate an exterior view of an implant loading system for a ventricular partitioning device, in accordance with a preferred embodiment;

FIGS. 9A-9C illustrate a cross-sectional view of an implant loading system for a ventricular partitioning device, in accordance with a preferred embodiment;

FIGS. 10A-10D illustrates an implant loading system for a ventricular partitioning device, in accordance with an alternative preferred embodiment;

FIG. 12 describes a method of using a delivery system for a ventricular partitioning device, in accordance with a preferred embodiment.

DETAILED DESCRIPTION

Disclosed herein are systems and devices for treating cardiac dysfunction. In some instances, cardiac dysfunction may include diastolic dysfunction, mitral valve regurgitation, and/or heart failure.

In general, the systems and devices described herein may be used to treat a patient's heart suffering from heart failure. The systems and devices may be used to treat a patient's heart experiencing diastolic dysfunction or a condition exhibiting characteristics of diastolic dysfunction, and may involve implanting within a ventricle of the heart a device that partitions the ventricle into functional and nonfunctional portions. In some embodiments, the device may deform during systole and recoil during diastole to supplement the natural elastic recoil action of the ventricle. In some embodiments, the device may reduce the end-diastolic volume, end-diastolic pressure, and/or increase the ejection fraction.

Diastole represents the period of time in the heart cycle in which the ventricles are relaxed and not contracting. Throughout most of diastole, blood is passively flowing from the right and left atria into the right and left ventricles, respectively. As the ventricles begin to contract, the pressure in the ventricles exceeds that of the atria, and the mitral valve closes, ending diastole. At this time, the ventricular pressure and volume are referred to as end-diastolic pressure and end-diastolic volume, respectively.

Reduced ventricular compliance, for example due to an increased stiffness in the ventricular heart wall, may result in increased end-diastolic pressure and decreased end-diastolic volume. Diastolic dysfunction may also result from changes in left ventricle relaxation during diastole. For example, inotropic stimulation, fast heart rates, non-uniform heart activation, and altered timing of forces that oppose ventricular ejection may contribute to altered left ventricle relaxation.

Devices

Figure 1:
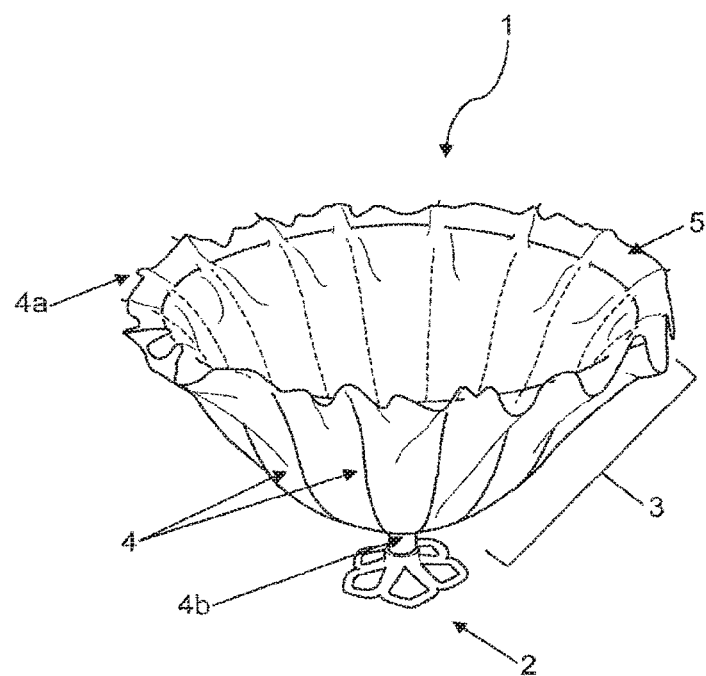
FIG. 1 illustrates a ventricular partitioning device in accordance with a preferred embodiment.

FIG. 1 illustrates an expandable device, which may also be referred to as a ventricular partitioning device, 1 to treat cardiac dysfunction. In some embodiments, cardiac dysfunction may include diastolic dysfunction, mitral valve regurgitation, heart failure, and/or any other type of malady of the heart. The device may be delivered to the ventricle of a patient to treat cardiac dysfunction. In some embodiments, as shown in FIG. 1, a device for treating cardiac dysfunction may include a foot 2 for contacting a first interior wall portion of a heart. Further, in some embodiments, a device for treating cardiac dysfunction may include a support frame 3 including a plurality of radially expandable struts 4 and a membrane 5 coupled to the support frame 3. Each of the radially expandable struts 4 has a first free end 4a and a second end 4b coupled to the foot 2.

FIGS. 2A-2D and 3A-3C illustrate a foot 2 coupled to a stem 6 of an expandable device in accordance with a preferred embodiment and an alternative preferred embodiment, respectively. The foot 2 of a ventricular partitioning device may contact an interior wall portion of a heart of a patient experiencing cardiac dysfunction. An interior wall portion of a heart may include an apex of a ventricle. In some embodiments, the foot 2 may contact the apex of the ventricle so that the entire device is underneath the papillary muscle located in the ventricle, such that the ventricular partitioning device does not interfere with the heart valve in the apex of the ventricle. In some embodiments, the foot 2 may contact the apex of the ventricle atraumatically such that the apex of the ventricle does not incur damage, trauma, and/or significant injury.

The foot 2 of the device, as shown in FIGS. 2A-3C, is supportive such that it does not collapse upon itself once implanted. However, the foot 2 may also be flexible, such that the device does not create focal pressure points (e.g., "hot spots") in the ventricle. To balance these properties of the ventricular partitioning device, the foot 2 of the ventricular partitioning device may include a thermoplastic elastomer. In some embodiments, the foot 2 may include thermoplastic silicone polyether polyurethane (TPU), such as DSM.

In some embodiments, as shown in FIGS. 2A-3C, the foot 2 may include a different material and/or durometer than the stem. In some embodiments, the foot 2 may include, Pursil TSPU, or any other thermoplastic material, such that the durometer is 70 A to 90 A, preferably 78 A to 84 A, and the flexural modulus or bending modulus is 15 MPa to 45 MPa, preferably 20 MPa to 40 MPa. In some embodiments, the stem 6 may include, elasthane TPU, or any other thermoplastic material, such that the durometer is 45 D to 75 D, preferably 50 D to 70 D, and the flexural modulus or bending modulus is 100 MPa to 400 MPa, preferably 145 MPa to 390 MPa.

In some embodiments, the foot 2 of the ventricular partitioning device may include a radiopaque filler material to aid in visualization of the implant during and/or after implantation of the ventricular partitioning device in the heart of a patient. In some embodiments, the foot 2 may include 20% radiopaque filler. Alternatively, the foot 2 and stem 6 may include 40% radiopaque filler and any other percent of radiopaque filler suitable to the application. For example, the foot 2 and/or stem 6 may include between about 10 and 50% radiopaque filler, or at least about 10, 20, 30, or 40% radiopaque filler.

In some embodiments, as shown in FIGS. 2C and 3C, the foot 2 may have a height H ranging from 0.5 mm to 4.0 mm and a diameter D ranging from 13 mm to 17 mm, depending on the distance between the apex of the ventricle and the papillary muscle in the ventricle. In some embodiments, the foot 2 of the ventricular partitioning device may comprise a plurality of sections or petals 7. In some embodiments, a foot 2 may include 1, 2, 3, 4, 5, 6, 7, 8, 9, or 10 petals, preferably 5 petals, as shown in FIGS. 2A, 2B, 3A, and 3C. The petals 7 may include a looped configuration such that each petal includes an aperture 7a. Alternatively, the petals may comprise a solid configuration. Each petal 7 may be coupled to at least two other petals 7 of the foot 2 of the ventricular partitioning device. Alternatively, each petal 7 of the foot 2 may be separate and uncoupled from the other petals 7 of the foot 2. In some embodiments, the foot may alternatively include a screw for securing the ventricular partitioning device to the apex, a hub, or any other component suitable for positioning a ventricular partitioning device in a heart.

In some embodiments, as shown in FIGS. 2A, 2C, and 2D, the petals 7 of the foot 2 may be curved or include an angled portion 8, such that the point of attachment 9 of the petals 7 to the stem 6 is held at a distance from the apex of the ventricle while the perimeter 10 of the petals 7 is contacting the apex of the ventricle, as shown in FIGS. 2A and 2B. Alternatively, as shown in FIGS. 3A and 3C, the petals 7 may be coupled to the stem 6 at a right angle (90°) to the stem 6, such that the entire perimeter 10 and/or surface area of the petals 7 of the foot 2 may contact the apex of the ventricle.

In some embodiments, as shown in FIGS. 3A-3C, the foot 2 may be used in a ventricular partitioning device for treating acute myocardial infarction in order to prevent cardiac remodeling or damage (configured as an endocardial implant). In this embodiment, the device is configured to be positioned immediately adjacent to the heart wall, for example similar to a patch, across from the region of the infarct.

FIGS. 2A-3C illustrate a stem 6 coupled to a foot 2 of a ventricular partitioning device, such that the stem 6 is configured to receive a support frame of a ventricular partitioning device, as shown in FIG. 1. In some embodiments, the stem 6 may be substantially rigid for coupling to the support frame. However, the stem 6 may also be flexible for increasing the elastic recoil force of the ventricular partitioning device. The stem 6, as shown in FIGS. 4A-4C, may include a base 11 and a shaft 12 for receiving a support frame. In some embodiments, as shown in FIG. 4A, the base 11 may include a flange 11a to create a strong bond between the stem 6 and the foot 2 of the ventricular partitioning device. For example, the petals of the foot may be injection molded around the base of the stem and flange. Alternatively, in some embodiments, the stem 6 may be coupled to the foot 2 by another mechanism, for example by screwing, soldering, sintering, snapping, locking, fastening, or any other type of reversible or irreversible coupling mechanism.

FIGS. 4B-4C illustrate a cross-section of a stem 6 of a ventricular partitioning device in accordance with a preferred embodiment. The stem 6 may serve as an interface between the foot 2 and the support frame 3 of the ventricular partitioning device. As shown in FIG. 4C, the foot 2 may be secured to the support frame 3 by a cross pin 13 or any other type of fastener. For example, the hub or shaft at the base of the support frame may slide over the shaft 12 of the stem 6, such that a pin 13 may be inserted through the cross-section of the stem 6 to couple the support frame 3 to the stem 6. Alternatively, the support frame may be soldered, fastened, glued, or otherwise reversibly or irreversibly coupled to the stem. In some embodiments, the shaft 12 of the stem 6 may be configured to receive a delivery catheter, as described below in association with FIG. 10. For example, the shaft 12 may include helical grooves 14 such that a shaft of the delivery catheter may be screwed into the shaft of the stem 6, as shown in FIGS. 2D, 4B, and 4C.

Figure 5A:
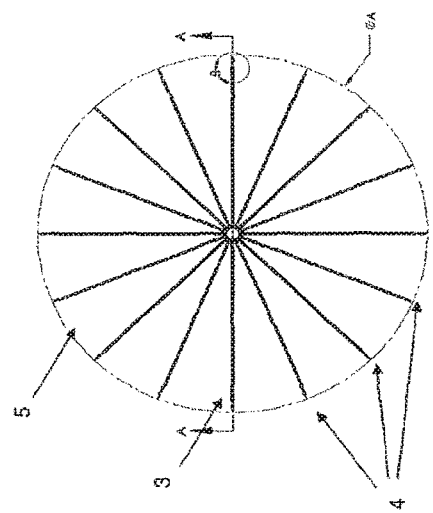
FIGS. 5A and 5B illustrate a top and side view of a membrane coupled to a support frame of a ventricular partitioning device, respectively, in accordance with a preferred embodiment.
Figure 5B:
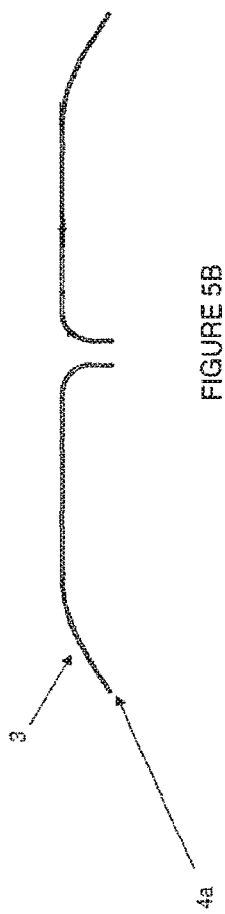

FIGS. 5A and 5B illustrate a top view and side view, respectively, of a membrane 5 coupled to a support frame 3 of a ventricular partitioning device in accordance with a preferred embodiment. The membrane 5 coupled to the support frame 3 is a pressure-receiving surface of the ventricular partitioning device, such that the elastic recoil force of the ventricle is improved when the ventricular partitioning device is implanted. The membrane 5 may be stretched over the struts to give the frame a disk like shape. The membrane 5 may include expanded Polytetrafuoroethylene (ePTFE) having a thickness between 0.01 mm and 1 mm, preferably about 0.08 mm. Alternatively, in some embodiments, the membrane 5 may include mesh, or other appropriate permeable, semi-permeable, or impermeable membranes. In some embodiments, the membrane 5 may be formed of a suitable biocompatible polymeric material including Nylon, PET (polyethylene terephthalate) and polyesters such as Hytrel. In some embodiments, the membrane 5 may be porous to facilitate tissue ingrowth after deployment within a patient's heart.

As shown in FIG. 5B, the first free ends 4a of the support frame 3 coupled to the membrane 5 may deflect away from the centerline axis of the ventricular partitioning device when the ventricular partitioning device is deployed in a ventricle. The deflection may improve the anchoring of the ventricular partitioning device to an interior wall of a ventricle.

In some embodiments, as shown in FIGS. 5A, 6A, and 6B, the support frame 3 may include a plurality of radially expandable struts 4. The struts 4 may be configured to support a membrane 5 coupled to the struts. The struts 4 may improve the elastic recoil properties of the membrane 5 coupled to the struts 4. In some embodiments, the struts 4 may be configured for anchoring the ventricular partitioning device to an interior wall of the ventricle. In some embodiments, the support frame 3 may include 5 struts, 10 struts, 15 struts, or 20 struts, preferably 16 struts. In some embodiments, each strut 4 may be 1 to 8 cm in length, preferably 3 to 6 cm. In some embodiments, the support frame 3 may be smoothed to a particular surface roughness to reduce trauma to the patient during delivery and improve characteristics of the ventricular partitioning device, such as corrosion resistance and durability. The support frame 3 may be electropolished, chemically treated, and/or mechanically polished by a wheel, tumbling, abrasion, sand blasting, chemical etching, and/or any other method of polishing to achieve a particular surface roughness. In some embodiments, the roughness average (Ra) of the support frame may be between 0.01 μm and 1 μm, preferably between 0.85 μm and 0.15 μm.

In some embodiments, as shown in FIGS. 6A-6C, each strut 4 of the support frame 3 may include a first free 4a end and a second end 4b coupled to the foot. The first free end 4a of the support frame 3 may include an anchor or barb 15 for coupling the support frame 3 to an interior wall portion of a heart. This anchoring may allow the ventricular partitioning device to contract and relax with each systolic and diastolic phase, respectively, of the heart cycle. Further, the anchoring may partition the heart into functional and non-functional portions, such that the non-functional portion is proximal to the foot of the ventricular partitioning device.

In some embodiments, as shown in FIGS. 6A-6C, a stop 16 may be located at or near the base of the anchors 15 proximal to the first free end 4a of the struts 4. The stop 16 may be a bulge, projection, or otherwise widening of a portion of the strut 4 near the first free end 4a, which serves to lock the support frame 3 in place and/or reduce or prevent over-penetration of the struts 4 into the ventricle wall. The length of the struts 4 may alternate between a short length strut and a long length strut so that the anchors 15 and/or stops 16 are staggered, which allows the struts 4 to be collapsed into a more compact diameter for delivery.

In some embodiments, as shown in FIG. 6A, each first free end 4a of the strut 4 of the support frame 3 may further include an eyelet 16a. The eyelet 16a may serve as a stop 16, as described above, and/or as a mechanism to couple the membrane to the support frame. During manufacturing, polymer may be melted near the eyelet 16a of the support frame 3 to couple the membrane to the support frame, such that the melted polymer may flow from one side of the strut 4 through the eyelet 16 to the other side of the strut 4 to couple the membrane to the struts 4. As shown in an alternative embodiment in FIGS. 6B-6C, the stop 16, as described above, may be manufactured without an eyelet, such that the polymer melts around the stop 16 and secures the membrane to the support frame 3.

Figure 7B:
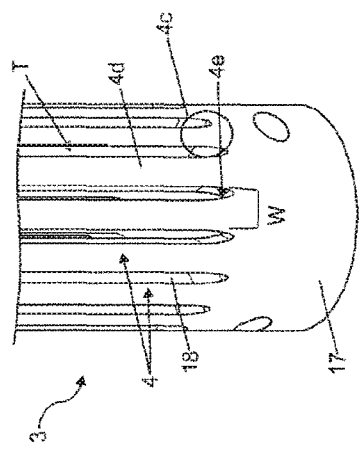
Figure 7A:
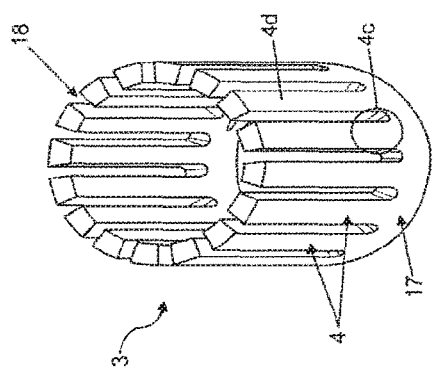

In some embodiments, as shown in FIGS. 7A-7D, the struts may include a material such as, for example, Nitinol, stainless steel, titanium alloys, NiTi alloy, other metal alloys, or plastic composites. In some embodiments, the struts 4 and/or support frame 3 may include a material, which allows for compression of the first free ends towards the central axis during delivery and self expansion upon deployment of the ventricular partitioning device in a patients heart. In some embodiments, the struts 4 and/or support frame 3 may be cut, for example by a laser, from a tube including Nitinol, stainless steel or a similar material. During manufacturing, a plurality of longitudinal cuts may extend from one end of the metal tube to a position offset from the other end of the tube, leaving a hub 17 from which the struts 4 extend. The cuts may result in a plurality of slots 18 between the struts 4. In some embodiments, as shown in FIG. 7A, the spacing between the slots 18 may define the strut width W while the thickness of the tube may define the strut thickness T. In some embodiments, the spacing of the slots 18 around the tube may result in struts 4 having a cross-sectional width that is slightly greater than its cross-sectional thickness. This may be accomplished by the slot 18 having a slightly greater spacing than the thickness of the tube. In some embodiments, slightly greater may mean about 1, 2, 3, 4, 5, 10, 15, 20, or 25 percent, or may mean between about 1 to 25 percent, or may mean between about 5 to 20 percent.

In some embodiments, as shown in FIG. 7B, the base 4c of the strut 4 is the second end of the strut that couples to the foot and extends from the hub 17. The base 4c of the strut 4 may be flared such that the width of the strut 4 increases as it approaches the hub 17. In some embodiments, the flared base 4c may spread bending strains over a larger amount of material, thereby decreasing peak strains during manufacturing, loading of the implant within a catheter, and cyclical use in the ventricle after implantation. In some embodiments, the width of the strut 4 at the hub 17 may be about 5 to 25 percent larger than the width of the strut 4 at a middle portion of the strut 4. In some embodiments, the length of the flared base 4c may be about equal to the width of the flared base 4c at the hub 17. Alternatively, the length of the flared base 4c may be greater than about 5, 10, 15, 20, 25, 30, 35, 40, 45, 50, 75, 100, or 200 percent of the width of the flared base 4c at the hub 17. Alternatively, the length of the flared base 4c may be less than about 95, 90, 85, 80, 75, 70, 65, 60, 55, or 50 percent of the width of the flared base 4c at the hub 17. The flared base may be formed by tapering the slot as it reaches the hub.

As illustrated in FIG. 7C, in some embodiments, the flared base can have a base bend radius 19 that is sized to (1) reduce or limit peak strains during shape setting to reduce or prevent damage and cracking of the metal frame; (2) reduce or limit peak strains when the implant is loaded into the catheter and reduce or prevent plastic deformation of the metal; and (3) reduce or minimize the height of the implant. In some embodiments, the diameter of the support frame 3 in its free shape 3a can be slightly oversized relative to its laminated shape 3b so that the membrane will stay tight after lamination. For example, the support frame 3 can be oversized by about 3, 4, 5, 6, or 7 mm, or be oversized between about 2 to 10 mm. The lamination mold is designed to conform to the natural shape of the support frame 3 when it is reduced to the lamination diameter 3b. This ensures that the support frame 3 is free to move as designed with little or no alternating strain concentrations.

As shown in FIG. 7D, after lamination, them is a strut curvature 20 near the anchor on the free ends 4a of the struts 4 that is designed to optimize the angle of engagement with the left ventricle wall which improves retention of the implant in the left ventricle. In some embodiments, the strut curvature 20 has a radius of about 0.5 to 1.5 inches. In some embodiments, the angle of engagement is about 30 to 60 degrees.

In some embodiments as described above, the strut cross-section dimensions having a width slightly greater than the thickness, in conjunction with the flared base, may bias the strut so that it deflects outwardly without any significant twist. This may improve the strength of the struts and reduce strain.

System

Figure 11:
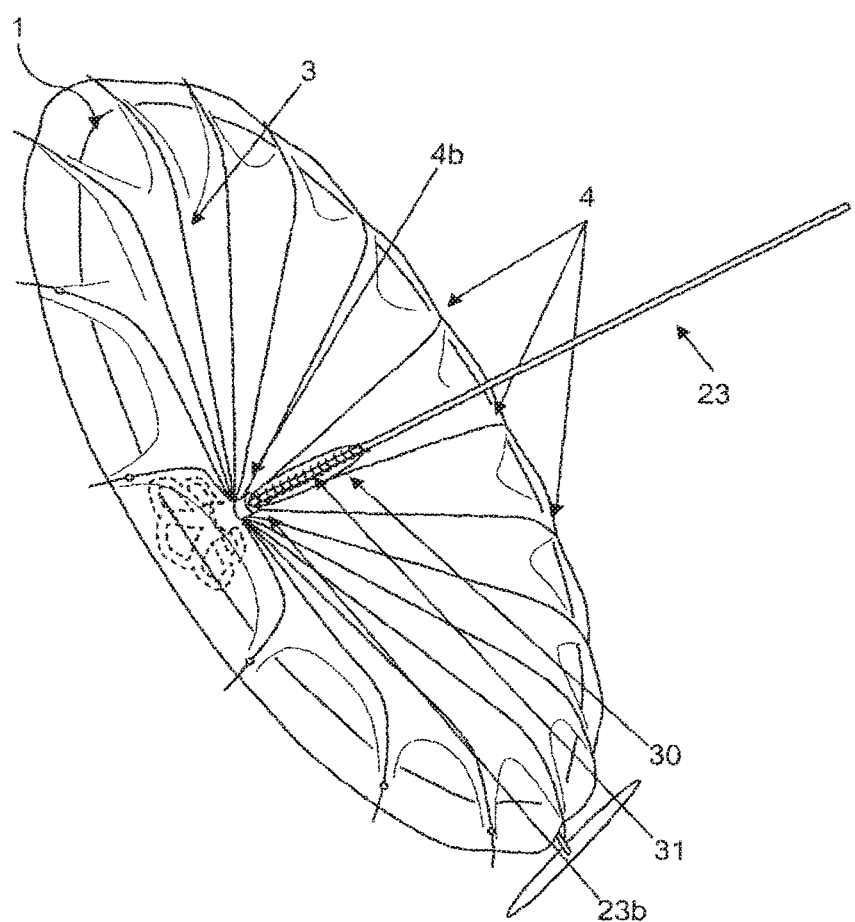
FIG. 11 illustrates a delivery catheter for a ventricular partitioning device, in accordance with a preferred embodiment.

In some embodiments, a delivery system for a ventricular partitioning device may include an implant loading system for collapsing the ventricular partitioning device into a substantially linear delivery configuration for passage into a delivery catheter and into a heart and expanding the ventricular partitioning device into an umbrella-like shape once the device is delivered into a heart. In some embodiments, the ventricular partitioning device may be delivered transapically, percutaneously, endovascularly, or through any other appropriate means or procedure. In some embodiments, the ventricular partitioning device is coupled to a shaft in a lumen of the delivery catheter, for example by screwing the ventricular partitioning device to a shaft in a lumen of the delivery catheter, as shown in FIG. 11.

Described below are two different embodiments of an implant loading system for loading a ventricular partitioning device into a delivery catheter. The system described in FIGS. 8A-9C is the preferred embodiment of the implant loading system. The system as shown in FIGS. 8A-9C requires fewer steps and components as compared to the implant loading system described in FIGS. 10A-10D. However, as evident to one of skill in the art, both implant loading systems may be used to load a ventricular partitioning device into a lumen of a delivery catheter for delivery to a heart of a patient.

In some embodiments, as shown in FIGS. 8A-9C, an implant loading system for a ventricular partitioning device may include a funnel 21 with a flared first end 21a and a second end 21b, wherein the flared first end 21a is configured for receiving a collapsed ventricular partitioning device 1, as shown in FIGS. 8B and 8D, and a sleeve 22 removably coupled to the second end 21b of the funnel 21, such that the sleeve 22 is configured to transfer the ventricular partitioning device 1 to a guide catheter, as shown in FIGS. 8C and 8D.

FIGS. 8A-8D and 9A-9C illustrate an exterior and cross-sectional view, respectively, of an implant loading system for a ventricular partitioning device, in accordance with a preferred embodiment. As shown in FIGS. 8A-8D, a ventricular partitioning device 1 may be coupled to a delivery catheter, 23, as described below. The ventricular partitioning device 1 may be collapsed by drawing at least two sutures, strings, ties, or threads together, such that the diameter of the membrane and thus the ventricular partitioning device is reduced, and the ventricular partitioning device 1 is at least partially collapsed around the delivery catheter 23. In some embodiments, the at least two sutures may be coupled by a tab, such that both sutures may be tensioned and the ventricular partitioning device at least partially collapsed by manipulating the tab. In some embodiments, the ventricular partitioning device may be positioned in the flared first end 21*a* of the funnel 21 with the first free ends of the struts of the ventricular partitioning device entering the flared first end 21*a* of the funnel 21 followed by the foot 2 of the ventricular partitioning device, as shown in FIG. 8D. The funnel 21 may function to fully collapse the ventricular partitioning device for advancement into a lumen of a guide catheter. In some embodiments, as shown in FIG. 8A, the second end 21*b* of the funnel 21 is removably coupled to a second end 22*b* of a sleeve 22, for example by threading 24 the funnel 21 onto the second end 22*b* of the sleeve 22, as shown in FIGS. 8A and 8C. In some embodiments, as shown in FIGS. 9A and 9C, the threads 24 for coupling the funnel 21 to the sleeve 22, as shown in FIG. 9B, are evident using a cross-sectional view of the funnel 21 and sleeve 22. Alternatively, the funnel 21 may be coupled to the sleeve 22 by any suitable mechanism. In some embodiments, the ventricular partitioning device coupled to the delivery catheter 23 may be advanced through the funnel 21 into the sleeve 22 for loading of the ventricular partitioning device into a lumen of a guide catheter. The first end 22*a* of the sleeve 22 may include a stop or tapering of the sleeve, such that the ventricular partitioning device does not protrude from the first end 22*a* of the sleeve 22 or extend out of the first end 22*a* of the sleeve 22, as shown in FIGS. 8A-8C. In some embodiments, the interior of the funnel 21 and sleeve 22 may include a smooth surface, for example without flashes or burrs, such that the ventricular partitioning device is not torn or scratched during loading, unloading, and advancing.

Once, the ventricular partitioning device is advanced into the sleeve 22 from the funnel 21, the funnel 21 may be uncoupled from the sleeve 22. In some embodiments, the second end 22*b* of the sleeve 22 may be coupled to a guide catheter using a dilator, such that the dilator may be rotated to increase or decrease the size of the aperture in the dilator. The ventricular partitioning device may be advanced from the sleeve into the lumen of the guide catheter. In some embodiments, the delivery catheter 23 coupled to the ventricular partitioning device may be advanced through the guide catheter lumen into a heart of a patient to position the ventricular partitioning device in the heart of the patient. In some embodiments, the sleeve may be removed from the delivery catheter by any suitable mechanism after advancing the ventricular partitioning device into the lumen of the guide catheter. Alternatively, the delivery catheter may be lengthened such that the sleeve may remain on the delivery catheter while the ventricular partitioning device is being positioned in a heart of a patient.

Alternatively, in some embodiments as shown in FIGS. 10A-10D, an implant loading system for a ventricular partitioning device may further include a loader 24 comprising a lumen housing a two-piece introducer 25, referred to herein as a loader introducer pair. Instead of a two-step loading procedure, as shown in FIGS. 8A-9C, the loading procedure shown in FIGS. 10A-10D includes at least two more steps. In some embodiments, as show in FIG. 10A, the funnel 26 for loading the ventricular partitioning device into the sleeve 27 may be truncated as compared to the funnel 21 shown in FIG. 8B. Similar to FIGS. 8A and 8D, the tapered end 26*b* of the funnel 26 may be coupled to the second end 27*b* of the sleeve 27 and the ventricular partitioning device coupled to the delivery catheter may be advanced from the funnel 26 into the sleeve 27. In some embodiments, as shown in FIG. 10C, once the ventricular partitioning device is collapsed and advanced through the funnel 26 into the sleeve 27, the funnel 26 may be uncoupled from the second end 27*b* of the sleeve 27 and the second end 24*b* of the loader introducer pair 24/25 may be coupled to the second end 27*b* of the sleeve 27. The loader introducer pair 24/25 may be coupled to the sleeve 27 by a helical screw, latching, snapping, fastening, or any other type of coupling mechanism. The first end 24*a* of the loader introducer pair 24/25 may be coupled to a guide catheter, such that the lumen of the loader introducer pair is continuous with the lumen of the guide catheter. In some embodiments, as shown in FIG. 10C, the coupling mechanism may include a slot 28 on the loader 24 and a pin, knob, protrusion, or port on the guide catheter, such that the slot 28 receives the pin or port and secures the loader 24 to the guide catheter. Alternatively, the loader 24 may be coupled to the guide catheter by a helical screw, snapping, latching, or any other type of coupling mechanism.

As shown in FIG. 10C, the ventricular partitioning device may be advanced from the sleeve 27 into the loader introducer pair 24/25 and into the guide catheter. The loader 24 may be removed from the system by moving the introducer 25 and delivery catheter through a longitudinal slot 29 in the loader 24. The introducer 25 may be removed from the system by tearing or axially pulling apart the two halves 25*a*/25*b* of the introducer 25, as shown in FIG. 10D, such that the delivery catheter coupled to the ventricular partitioning device in the lumen of the guide catheter remains. In some embodiments, the sleeve 27 may remain on the delivery catheter or be removed. While two embodiments of an implant loading system are described above, any other suitable mechanism may be used and/or substituted by one skilled in the art to deliver a ventricular partitioning device to a heart of a patient.

In some embodiments, as shown in FIG. 11, a system for treating heart failure may include a ventricular partitioning device as described above, and a delivery catheter 23 having a proximal end and a distal end 23*b*. Further, a system for treating heart failure may include an expansion member 30 near the distal end 23*b* of the delivery catheter 23 configured to apply pressure to the support frame 3 of the ventricular partitioning device 1 to move the ventricular partitioning device 1 from a collapsed delivery configuration to an expanded deployed configuration, and a coupling element 31 configured to secure the expansion member 30 to the ventricular partitioning device 1 during deployment.

In some embodiments, the delivery catheter 23 may include a useable length between 120 cm and 170 cm, preferably 125 cm or 155 cm. In some embodiments, the delivery catheter 23 may include an outer diameter between 5 Fr and 14 Fr, preferably 10 Fr (3.3 mm).

In some embodiments, the expansion member 30 is coupled to the ventricular partitioning device 1 by a coupling element 31 proximal to the second ends 4*b* of the struts 4 of the support frame 3. In some embodiments, the coupling element 31 includes a helical screw, as shown in FIG. 11. Alternatively, in some embodiments, the coupling element 31 may include a sliding latch, lock, hook, or any other suitable mechanism. In some embodiments, the expansion member 30, for example a balloon, may be in fluid communication with a lumen in the shaft of the delivery catheter 23, such that inflation fluid may be delivered to the interior of the expansion member 30 to inflate the balloon. Alternatively, the balloon may be inflated by a gas, gel, or any other material. The balloon, once inflated, may include a diameter between 30 mm and 45 mm, preferably more than or equal to 32 mm.

In some embodiments, the ventricular partitioning device 1 radially expands in the ventricle once delivered to the ventricle. The expansion member 30, coupled to the ventricular partitioning device 1 by a coupling element 31, may be inflated at the distal end of the delivery catheter 23 to fully expand the ventricular partitioning device 1 within the ventricle and to facilitate anchoring the struts 4 of the ventricular partitioning device to an interior wall of the ventricle. Alternatively, in some embodiments, the ventricular partitioning device 1 may expand and anchor sufficiently without the use of the expansion member 30. In some embodiments, rotation of the delivery catheter 23 coupled to the ventricular partitioning device 1 may remove the expansion member 30 and delivery catheter 23 from the ventricular partitioning device 1.

In some embodiments, as shown in FIG. 12, a method of delivering a ventricular partitioning device comprises positioning with a delivery catheter an expandable partitioning device near an apex of a patient's ventricle, such that the expandable partitioning device includes a membrane coupled to a plurality of expandable struts S100; expanding an expansion member coupled to the partitioning device to apply pressure to the plurality of expandable struts to expand the partitioning device S110; and removing the expansion member from the partitioning device to deploy the partitioning device S120. In some embodiments, a method of delivering a ventricular partitioning device may further include loading the partitioning device into a guide catheter through a funnel and a sleeve. In some embodiments, a method of delivering a ventricular partitioning device may further include uncoupling a coupling element from the partitioning device to release the partitioning device from the delivery catheter. In some embodiments, a method of delivering a ventricular partitioning device may further include positioning a delivery sheath over the partitioning device to collapse the partitioning device for removal or redeployment of the partitioning device.

Manufacturing

As described above and as shown in FIGS. 6A and 6B, the struts 4 of the support frame 3 of a ventricular partitioning device are cut, for example, by a laser, from a metal tube, for example Nitinol. In some embodiments, a method for securing a membrane 5 to struts 4 of a support frame 3 includes providing the support frame 3 including a plurality of struts 4; positioning the support frame 3 within a first platen structure having a male shaping portion and a second platen structure having a female shaping portion; positioning a membrane, for example a polymeric sheet, on the support frame 3 within the first and second platen structures; pressing the first and second platen structures together; and heating the first and second platen structures housing the support frame 3 and the polymeric sheet to fuse the polymeric sheet to the support frame. In some embodiments, fusion may occur by heating and reforming of the thermoplastic material to the polymeric sheet.

In some embodiments, positioning the support frame 3 within a first platen structure includes slidably disposing tubes over the struts 4 of the support frame 3 and positioning the support frame 3 in the female platen structure on top of a membrane 5, such that the membrane 5 is sandwiched between the female platen and the support frame 3. In some embodiments, the tube disposed over the struts 4 of the support frame 3 may include a thermoplastic material or any other suitable material. In some embodiments, the membrane 5 includes a centrally located aperture configured to receive the hub 17 of the struts 4 of the support frame 3. In some embodiments, a second membrane may be positioned on top of the support frame, forming a bilaminar structure. A male platen may be positioned on the membrane 5 and support frame 3 on the female platen structure, such that the male and female platens are coupled and may be heated and pressed to couple the membrane 5 to the support structure 3. Alternatively, in some embodiments, the membrane 5 and support frame 3 may first be positioned in a male platen and the female platen may be secondarily positioned on the male platen and heated and pressed to couple the membrane 5 to the support structure 3.

In some embodiments, pressing and heating the male and female platens together may include pressing, clamping, compaction plus sintering, hot isostatic pressing, compression molding, and/or any other method known to one skilled in the art. The melting point of the thermoplastic material is lower than that of the membrane material, for example, ePTFE, such that the application of heat and pressure, as detailed above, is sufficient to melt the thermoplastic material but does not cause melting of the ePTFE membrane.

The examples and illustrations included herein show, by way of illustration and not of limitation, specific embodiments in which the subject matter may be practiced. Other embodiments may be utilized and derived therefrom, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is in fact disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other EMBODIMENTS not specifically described herein, will be apparent to those of skill in the art upon reviewing the above description.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc.

Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that the throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

What is claimed is:

1. An implant loading system comprising:
a funnel for loading an expandable implant into a catheter for delivery to a heart, the funnel having a flared first end and a second end, wherein the flared first end comprises a tapering receptacle for receiving and collapsing the expandable implant, and a second portion at the second end comprises a lumen, the second end including a coupling element for removably coupling the funnel to a sleeve; and a sleeve configured to be removably coupled to the second end of the funnel and having a coupling element located in a center portion of the sleeve for mating with the coupling element at the second end of the funnel, the sleeve including a tubular portion distal to the coupling element of the sleeve that is configured to be positioned within the second portion of the funnel.

2. The implant loading system of claim 1, wherein the lumen of the second portion has a first diameter, and the sleeve has a lumen with a second diameter that is less than the first diameter.

3. The implant loading system of claim 2, wherein the tubular portion of the sleeve distal to the coupling element of the sleeve has the second diameter.

4. The implant loading system of claim 1, wherein the tubular portion of the sleeve distal to the coupling element of the sleeve has a lumen that is configured to receive the expandable implant from the funnel.

5. The implant loading system of claim 1, wherein the sleeve includes a tubular portion proximal to the coupling element of the sleeve.

6. The implant loading system of claim 1, wherein the tubular portion of the sleeve distal to the coupling element of the sleeve extends distal from the second end of the funnel when the funnel and the sleeve are coupled together.

7. The implant loading system of claim 1, wherein the funnel is configured to collapse the expandable implant for advancement into the tubular portion of the sleeve.

8. The implant loading system of claim 1, wherein the funnel is configured to collapse the expandable implant for advancement into a lumen of the catheter.

9. The implant loading system of claim 1, wherein an interior of the funnel includes a smooth surface.

10. The implant loading system of claim 1, wherein the funnel is configured to be uncoupled from the sleeve following the expandable implant being advanced into a lumen of the sleeve.

11. The implant loading system of claim 1, wherein the coupling element of the sleeve is positioned upon an outer surface of the sleeve.

12. The implant loading system of claim 1, wherein the coupling element of the funnel is positioned upon an interior surface of the funnel.

13. The implant loading system of claim 1, further comprising the expandable implant.

14. The implant loading system of claim 13, wherein the expandable implant is for treating cardiac dysfunction.

15. The implant loading system of claim 13, wherein the expandable implant includes a support frame configured to be collapsed by the funnel.

* * * * *